United States Patent [19]

Uchida et al.

[11] Patent Number: 5,064,565
[45] Date of Patent: Nov. 12, 1991

[54] CYCLOHEXENYLETHANE COMPOUND

[75] Inventors: Manabu Uchida; Yasuyuki Goto, both of Ichihara, Japan

[73] Assignee: Chisso Corporation, Osaka, Japan

[21] Appl. No.: 549,138

[22] Filed: Jul. 5, 1990

[30] Foreign Application Priority Data

Jul. 26, 1989 [JP] Japan ............................ 1-191268
Apr. 6, 1990 [JP] Japan ............................ 2-90190

[51] Int. Cl.$^5$ .................... C09K 19/52; C09K 19/54
[52] U.S. Cl. .................... 252/299.001; 252/299.63; 252/299.5; 359/103
[58] Field of Search .............. 252/299.1, 299.63, 299.5; 570/129, 130, 182, 188; 350/350 R, 350 S

[56] References Cited

U.S. PATENT DOCUMENTS

| | | | |
|---|---|---|---|
| 4,405,488 | 9/1983 | Sugimori et al. | 252/299.63 |
| 4,606,845 | 8/1986 | Romer et al. | 252/299.63 |
| 4,797,228 | 1/1989 | Goto et al. | 252/299.63 |
| 4,820,443 | 4/1989 | Goto et al. | 252/299.63 |
| 4,871,470 | 10/1989 | Wachtler et al. | 252/299.63 |
| 4,910,350 | 3/1990 | Tanaka et al. | 570/129 |

FOREIGN PATENT DOCUMENTS

DE3717397A1 12/1988 Fed. Rep. of Germany .

WO88/06178 8/1988 PCT Int'l Appl. .

Primary Examiner—Robert L. Stoll
Assistant Examiner—Shean C. Wu
Attorney, Agent, or Firm—Wenderoth, Lind & Ponack

[57] ABSTRACT

A cyclohexenylethane compound is disclosed which is represented by the formula

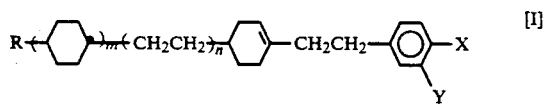

wherein R is an alkyl group having 1 to 10 carbon atoms, X is an alkyl group or an alkoxy group having 1 to 10 carbon atoms, a cyano group, a bromine atom or a fluorine atom, Y is a hydrogen atom or a fluorine atom, m is 0 or 1, and n is 0 or 1.

The above-mentioned cyclohexenylethane compound of the present invention exhibits a liquid crystal phase having a broad range, has a good compatibility with known liquid crystal compounds, can expand the liquid crystal temperature range of a liquid crystal composition, can expand the drive temperature range of a liquid crystal element, and is very stable to environmental factors.

11 Claims, No Drawings

CYCLOHEXENYLETHANE COMPOUND

BACKGROUND OF THE INVENTION

1. Field of the Invention

The present invention relates to a novel cyclohexenylethane compound, and more specifically, it relates to a novel cyclohexenylethane derivative which is suitable as one component of an electro-optical display material, and a liquid crystal composition containing this derivative.

2. Description of Related Art

In recent years, a liquid crystal has become more and more important as a dielectric for a display element because of an electro optical effect based on the anisotropy of a dielectric constant and a refractive index. As display systems for the liquid crystal, there are, for example, a dynamic scattering system, a phase transition system, a DAP system, a guest/host system, a TN system using a 90° twisted cell, an STN or SBE system using a 180°-270° twisted cell and an active matrix system using TFT to which much attention is paid of late. Liquid crystal materials used in these display systems are required to have various characteristics. For example, each liquid crystal material should have a wide temperature range in which a liquid crystal phase is maintained; it should be stable to environmental factors (e.g., moisture, heat, air, light and electricity); it should be colorless; its anisotropy quantity (hereinafter abbreviated as "Δn") of a refractive index should be a suitable value; its elastic constant ratio should be high (or low); its anisotropy quantity (hereinafter abbreviated as "Δε") of a dielectric constant should be large; its viscosity should be low; and its specific resistance ratio should be high and the change of this ratio with time should be slight.

Presently, however, no single compound can drive the display element sufficiently by itself, and in fact, a liquid crystal mixture prepared by mixing several kinds of liquid crystal-like compounds is used. For this reason, it is required that the liquid crystal-like compounds have a good compatibility with other liquid crystal compounds.

In this specification, the term "liquid crystal-like compound" means the liquid crystal compound or a compound having a certain function to drive the liquid crystal display element.

Nowadays, a compound having a cyclohexene ring has been introduced as the liquid crystal. For example, Japanese Laid-open Patent Publication No. 1-106830 and DE 3717397A1 disclose

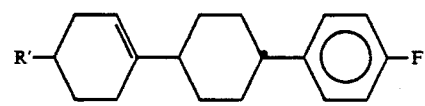

wherein R' is an alkyl group or the like, but in this compound, the upper limit temperature for the liquid crystal phase is low in spite of it being a tricyclic compound.

In addition, U.S. Pat. No. 4405488 discloses a compound represented by the formula

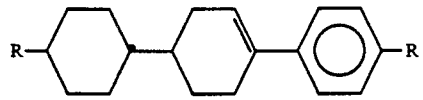

wherein R is an alkyl group, but this compound is unstable to environmental factors.

SUMMARY OF THE INVENTION

An object of the present invention is to provide a novel liquid crystal compound having a cyclohexene ring which can exhibit a liquid crystal phase having a broad range.

Another object of the present invention is to provide a novel liquid crystal compound having a cyclohexene ring which is excellent in compatibility with known liquid crystal compounds.

Still another object of the present invention is to provide a novel liquid crystal compound having a cyclohexene ring which can expand the liquid crystal phase temperature range of a liquid crystal composition.

A further object of the present invention is to provide a novel liquid crystal compound having a cyclohexene ring which can expand the drive temperature range of a liquid crystal element.

A still further object of the present invention is to provide a novel liquid crystal compound having a cyclohexene ring which is very stable to environmental factors.

A still further object of the present invention is to provide a liquid crystal composition containing at least one of these liquid crystal compounds.

According to one aspect of the present invention, there is provided a cyclohexenylethane compound represented by the formula [I]

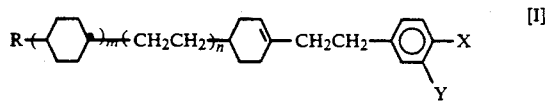

wherein R is an alkyl group having 1 to 10 carbon atoms, X is an alkyl group or an alkoxy group having 1 to 10 carbon atoms, a cyano group, a bromine atom or a fluorine atom, Y is a hydrogen atom or a fluorine atom, m is 0 or 1, and n is 0 or 1.

According to another aspect of the present invention, there is provided a liquid crystal composition comprising at least two components, at least one of these components being a cyclohexenylethane compound represented by the above-mentioned formula [I].

DESCRIPTION OF THE PREFERRED EMBODIMENTS

A cyclohexenylethane compound of the present invention is represented by the formula [I]

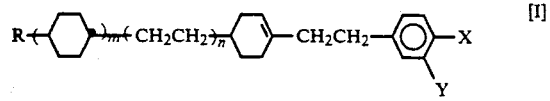

wherein R is an alkyl group having 1 to 10 carbon atoms, X is an alkyl group or an alkoxy group having 1 to 10 carbon atoms, a cyano group, a bromine atom or a fluorine atom, Y is a hydrogen atom or a fluorine atom, m is 0 or 1, and n is 0 or 1.

In the formula [I], the number of the carbon atoms in R is preferably from 1 to 7, more preferably from 1 to 5, and the number of the carbon atoms in the alkyl group or the alkoxy group of X is preferably from 1 to 6.

In the compound of the present invention in which the alkyl group of R, or the alkyl group or alkoxy group of X is a straight chain, liquid crystal characteristics are excellent and viscosity is conveniently low, and with regard to the compound of the present case in which the above-mentioned group is branched, its solubility in conventional liquid crystal materials is high. In particular, when the above-mentioned group (which preferably has at most one branched chain) is optically active, the compound of the present invention can be used as a chiral dopant.

The particularly preferable compounds represented by the formula [I] are as follows:

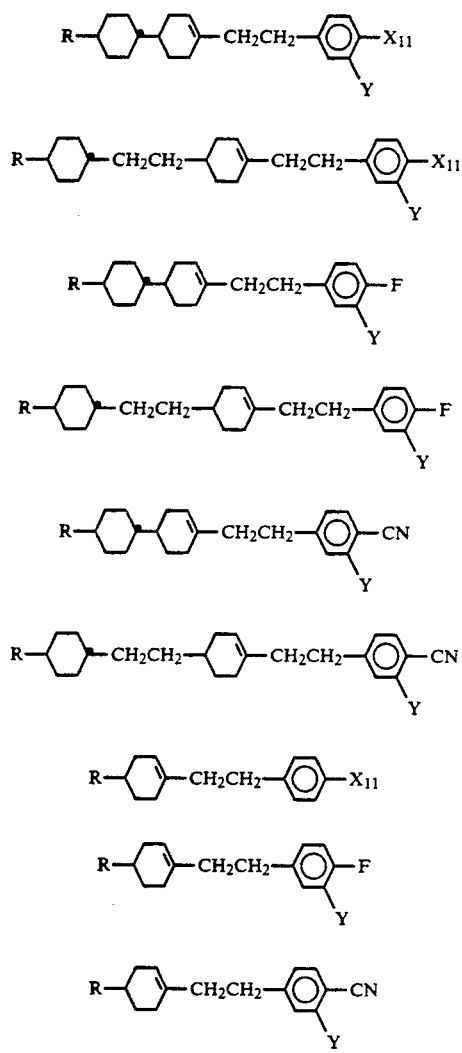

wherein R and Y are the same as in the formula [I], and $X_{11}$ is an alkyl group or an alkoxy group having 1 to 10 carbon atoms, preferably a straight-chain alkyl or alkoxy group having 1 to 6 carbon atoms.

Compounds represented by these formulae will be referred to in the undermentioned examples, and interrelations therebetween are as follows:

the compounds represented by the formula [Iaa] are referred to in Examples 1, 2, 5 and 6, the compounds represented by the formula [Iab] are referred to in Examples 3, 4, 7 and 8, the compounds represented by the formula [Iac] are referred to in Examples 9 and 10, the compounds represented by the formula [Iad] are referred to in Examples 11 and 12, the compounds represented by the formula [Iba] are referred to in Example 19, Example 20 (Compound Nos.345-352), Example 23, and Example 24 (Compound Nos.372-379), the compounds represented by the formula [Ibb] are referred to as Compound Nos. 353-361 in Example 20 and Compound Nos. 380-388 in Example 24, and the compounds represented by the formula [Ide] are referred to in Examples 13 and 14.

The cyclohexenylethane compound of the present invention shows a liquid crystal phase having a broad range. Furthermore, the compound is excellent in compatibility with other known liquid crystal compounds such as esters, Schiff's compounds, ethanes, acetylenes, azoxy compounds, biphenyls, cyclohexanes, cyclohexenes, pyridines, pyrimidines and dioxanes. Therefore, the cyclohexenylethane compound can be mixed with these compounds or a mixture thereof to form a liquid crystal material suitable for various applications.

One reason why the cyclohexenylethane compound is excellent in compatibility is that it has the cyclohexene ring in its molecule. Moreover, the cyclohexenylethane compound is very stable to environmental factors (e.g., moisture, heat, air, light and electricity), and the reason for this would be that an ethane bond is present between the cyclohexene ring and the benzene ring.

Of the compounds of the present invention, the compounds represented by the formulae [Iaa], [Iab], [Iba] and [Ibb] have high transparency and thus they permit driving the liquid crystal element at a high temperature. The compounds represented by the formulae [Iaa], [Iab] and [Iae] have low viscosities, and thus they permit heightening the response velocity of the liquid crystal element. The compounds represented by the formulae [Iba], [Ibb] and [Ibc] have a large positive Δε, and thus they permit the drive voltage of the liquid crystal element to decrease. The compounds represented by the formulae [Iac], [Iad] and [Iaf] have relatively large positive Δε's and are excellent in stability, and thus they are suitable for an active matrix system using TFT. Furthermore, the compounds represented by the formulae [Iac] and [Iad] are excellent, because they exhibit a liquid crystal phase in a desirable temperature range.

The compound of the present invention can be prepared by the following method (a) or (b).

(a) The compound represented by the formula [I] in which X is a group other than a cyano group can be synthesized as follows:

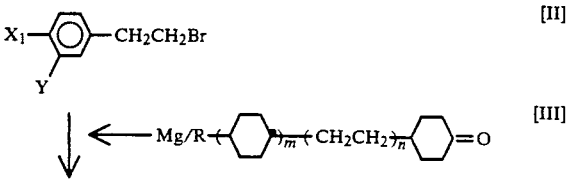

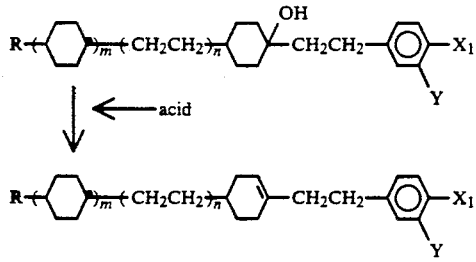

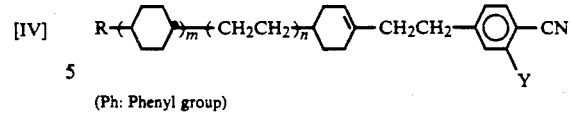

(Ph: Phenyl group)

wherein $X_1$ is a fluorine atom, an alkyl group or an alkoxy group having 1 to 10 carbon atoms, and R, Y, m and n are as defined above.

In the first place, a phenethyl bromide derivative [II] is reacted with magnesium in an ether or a THF solvent in order to prepare a Grignard reagent, and a cyclohexanone derivative [III] is added dropwise to the prepared reagent. In this case, no particular restriction is put on reaction temperature, but it is preferably in a range of from 0° to 50° C. Afterward, stirring is continued for a period of several hours, thereby obtaining a cyclohexanol derivative [IV]. Next, this derivative [IV] is reacted at a reflux temperature for several hours in the presence of an acid catalyst such as p-toluenesulfonic acid in a solvent such as toluene in order to obtain the cyclohexenylethane compound [Ia] which is the compound of the present invention.

(b) The compound represented by the formula [I] in which X is the cyano group can be synthesized as follows:

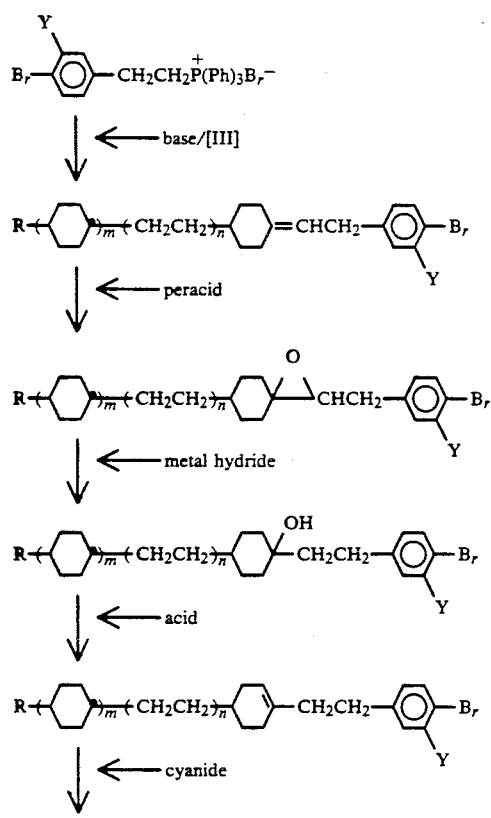

That is, a phosphonium salt [V] synthesized by a usual process is allowed to act on a base such as potassium tert-butoxide or n-butyl lithium, and then reacted with the cyclohexanone derivative [III]. The resulting compound [VI] is oxidized with a peracid such as meta-chloroperbenzoic acid to obtain an epoxide [VII]. Next, the latter is reduced with a metal hydride such as lithium aluminum hydride or lithium triethylboron hydride, and further dehydrated with an acid catalyst such as paratoluenesulfonic acid to form the cyclohexene derivative [Ic]. Afterward, the compound [Ic] is treated with a cyanide such as copper cyanide, thereby obtaining the desired cyclohexenylethane compound [Ib].

The liquid crystal composition of the present invention is characterized by containing at least two liquid crystal compounds or liquid crystal-like compounds, and also characterized in that at least one of these compounds is the liquid crystal-like compound represented by the above-mentioned formula (I).

Examples of the compounds usable as the component of the liquid crystal composition of the present invention which can be mixed with the compound of the formula [I] include known compounds represented by the following formulae (i) to (xxxiii):

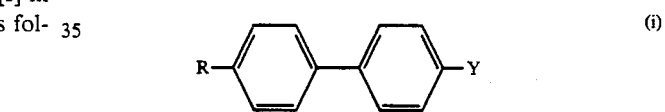

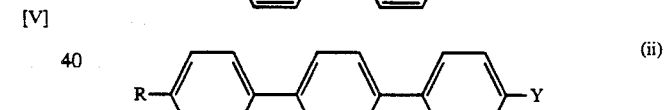

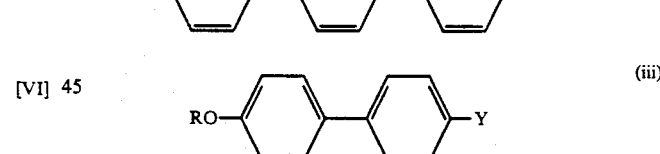

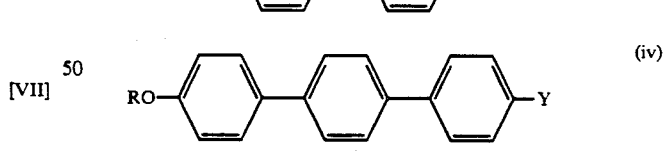

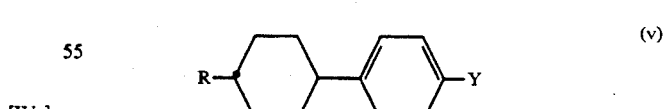

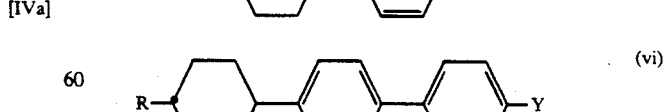

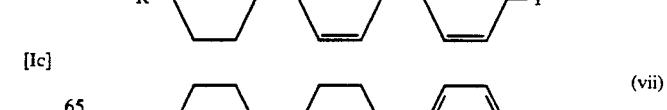

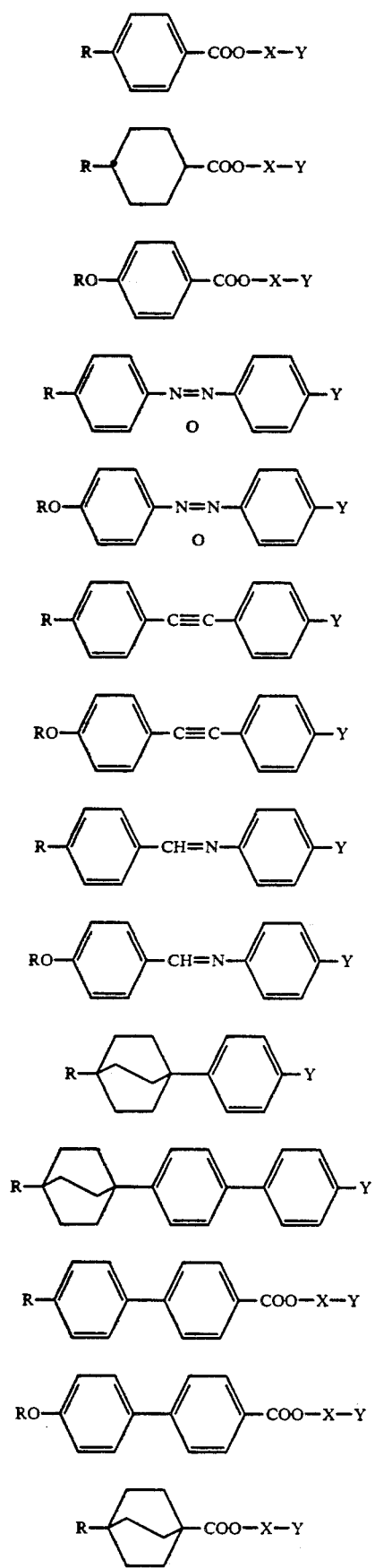
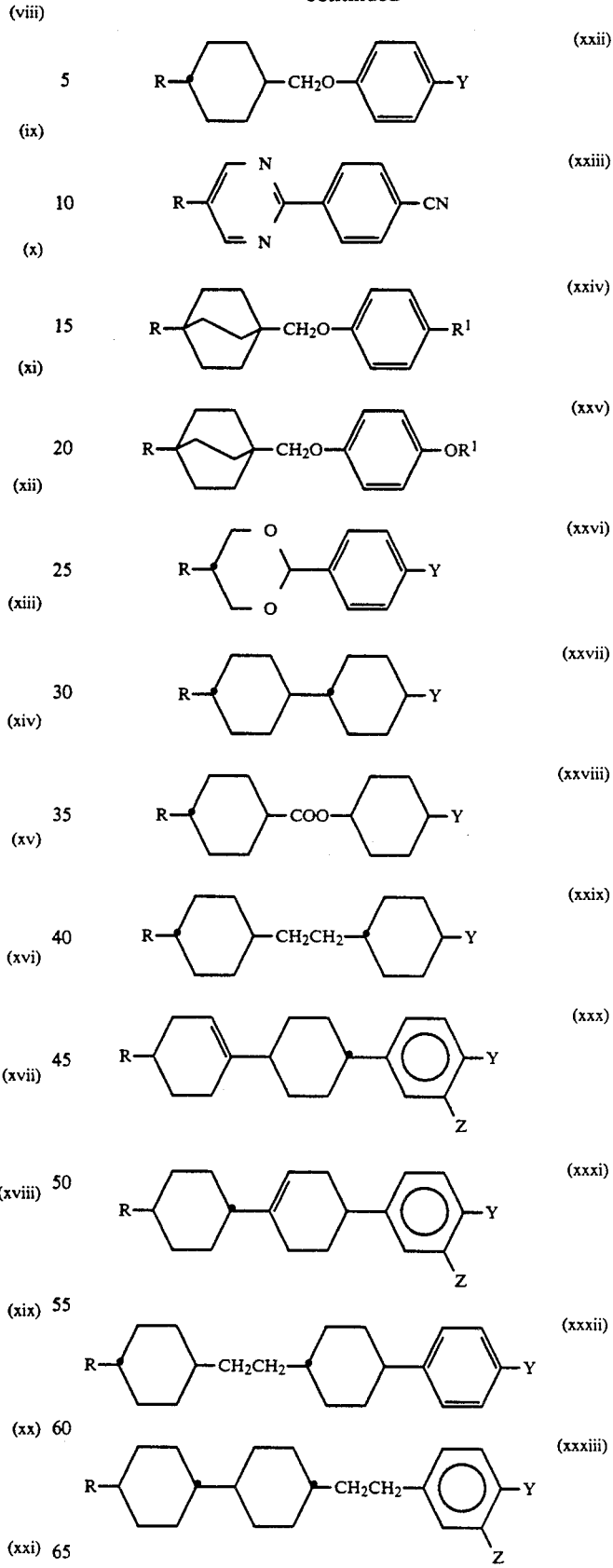
wherein X is

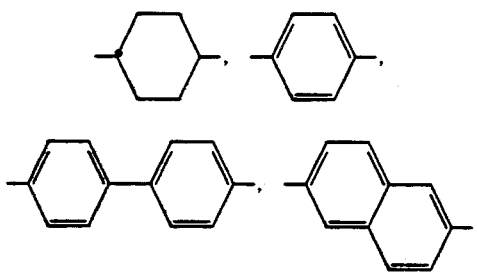

Y is -CN, -F, -CF$_3$, -OCF$_3$, R$_1$ or OR$_1$, Z is -H or -F, and each of R and R$_1$ is an alkyl group or an alkenyl group.

Now, the present invention will be described in more detail with reference to examples, but the scope of the present case should not be limited to these examples.

In the respective examples, symbols have the following meanings:

m.p.: melting point, and clp.: clearing point [each value in parentheses denotes a monotropic transition temperature]

EXAMPLE 1

Synthesis of 4-(trans-4-n-propylcyclohexyl)-[2-(4-methylphenyl)ethyl]cyclohexene [Compound No. 1 (in the formula [Iaa], X$_{11}$=methyl, Y=H, and R=n-propyl)]:

In a nitrogen gas stream, 30 ml of a THF solution containing 6.6 g of 2-(4-methylphenyl)ethyl bromide was added dropwise at 20° C. into a three-necked flask in which 0.9 g of magnesium and 5 ml of THF were present. Afterward, the solution was stirred for 1 hour, and 20 ml of a THF solution containing 6.7 g of 4-(trans-4-n-propylcyclohexyl)cyclohexanone was then added dropwise thereto at 20° C. After stirring for 5 hours, the solution was cooled to 0° C., and 50 ml of 6 N hydrochloric acid and 50 ml of toluene were then added thereto. After the removal of a water layer, the solution was washed with 50 ml of a 1 N aqueous sodium hydroxide solution, and water washing was continued until the aqueous solution had become neutral. The resulting toluene solution was dried over anhydrous magnesium sulfate and then concentrated. Afterward, 0.3 g of p-toluenesulfonic acid and 20 ml of toluene were added thereto, followed by heating under reflux for 1 hour. At this time, a drainage pipe was used to remove water formed by azeotropy. The solution was then cooled to 20° C., and 50 ml of a 0.5 N aqueous sodium hydroxide solution and 50 ml of heptane were added thereto, followed by removing a water layer. Afterward, the solution was washed with 50 ml of a saturated sodium chloride solution three times, and then dried over anhydrous magnesium sulfate and concentrated The thus treated solution was passed through an alumina-packed column by the use of a heptane solvent, and the used heptane was then distilled off, followed by distillation, whereby 6 2 g of white crystals was obtained. The thus obtained crystals were further recrystallized from a hexane solvent and then dried in order to prepare 3.2 g of the desired compound. The chemical structure of the product was confirmed by NMR.

m.p. 46° C. and clp. 120° C.

EXAMPLE 2

The same procedure as in Example 1 was effected except that 2-(4-methylphenyl)ethyl bromide used in Example 1 was replaced with a suitable phenetyl bromide derivative and 4-(trans-4-n-propylcyclohexyl)cyclohexanone was replaced with a suitable cyclohexanone derivative, thereby obtaining the following compounds (in the formula [Iaa], X$_{11}$=alkyl and Y=H).

Compound No. 2: 4-(trans-4-ethylcyclohexyl)-[2-(4-methylphenyl)ethyl]cyclohexene
m.p. 1° C. and clp. 91° C.

Compound No. 3: 4-(trans-4-n-butylcyclohexyl)-[2-(4-methylphenyl)ethyl]cyclohexene Compound No. 4: 4-(trans-4-n-pentylcyclohexyl)-[2-(4-methylphenyl)ethyl]cyclohexene
m.p. 36° C. and clp. 125° C.

Compound No. 5: 4-(trans-4-n-hexylcyclohexyl)-[2-(4-methylphenyl)ethyl]cyclohexene Compound No. 6: 4-(trans-4- ethylcyclohexyl) .[2-(4-ethylphenyl)ethyl]cyclohexene
m.p. 1° C. and clp. 107° C.

Compound No. 7: 4-(trans-4-n-propylcyclohexyl)-[2-(4-ethylphenyl)ethyl]cyclohexene
clp. 118° C.

Compound No. 8: 4-(trans-4-n-butylcyclohexyl)-[2-(4-ethylphenyl)ethyl]cyclohexene Compound No. 9: 4-(trans-4-n-pentylcyclohexyl)-[2-(4-ethylphenyl)ethyl]cyclohexene
clp. 127° C.

Compound No. 10: 4-(trans-4- n-hexylcyclohexyl)-[2-(4-ethylphenyl)ethyl]cyclohexene Compound No. 11: 4-(trans-4-n-ethylcyclohexyl)-[2-(4-n-propylphenyl)ethyl]cyclohexene Compound No. 12: 4-(trans-4-n-propylcyclohexyl)-[2-(4-n-propylphenyl)ethyl]cyclohexene
clp. 128° C.

Compound No. 13: 4-(trans-4-n-butylcyclohexyl)-[2-(4-n-propylphenyl)ethyl]cyclohexene Compound No. 14: 4-(trans-4-n-pentylcyclohexyl)-[2-(4-n-propylphenyl)ethyl]cyclohexene
m.p. 35° C. and clp. 138° C.

Compound No. 15: 4-(trans-4-n-hexylcyclohexyl)-[2-(4-n-propylphenyl)ethyl]cyclohexene Compound No. 16: 4-(trans-4- ethylcyclohexyl) -[2-(4-n-butylphenyl)ethyl]cyclohexene Compound No. 17: 4-(trans-4-n-propylcyclohexyl)-[2-(4-n-butylphenyl)ethyl]cyclohexene
clp. 129° C.

Compound No. 18: 4-(trans-4-n-butylcyclohexyl)-[2-(4-n-butylphenyl)ethyl]cyclohexene Compound No. 19: 4-(trans-4-n-pentylcyclohexyl)-[2-(4-n-butylphenyl)ethyl]cyclohexene
clp. 139° C.

Compound No. 20: 4-(trans-4-n-hexylcyclohexyl)-[2-(4-n-butylphenyl)ethyl]cyclohexene Compound No. 21: 4-(trans-4- ethylcyclohexyl) .[2-(4-n-pentylphenyl)ethyl]cyclohexene
clp. 103° C.

Compound No. 22: 4-(trans-4-n-propylcyclohexyl)-[2-(4-n-pentylphenyl)ethyl]cyclohexene
clp. 128° C.

Compound No. 23: 4-(trans-4-n-butylcyclohexyl)-[2-(4-n-pentylphenyl)ethyl]cyclohexene Compound No. 24: 4-(trans-4-n-pentylcyclohexyl)-[2-(4-n-pentylphenyl)ethyl]cyclohexene
m.p. 16° C. and clp. 141° C.

Compound No. 25: 4-(trans-4-n-hexylcyclohexyl)-[2-(4-n-pentylphenyl)ethyl]cyclohexene Compound No. 26: 4-(trans-4- ethylcyclohexyl) -[2-(4-n-hexylphenyl)ethyl]cyclohexene Compound No. 27: 4-(trans-4-n-propylcyclohexyl)-[2-(4-n-hexylphenyl)ethyl]cyclohexene Compound No. 28: 4-(trans-4-n-butylcyclohexyl)-[2-(4-n-hexylphenyl)ethyl]cyclohexene Compound No. 29: 4-(trans-4-n-pentylcyclohexyl)-[2-(4-n-hexylphenyl)ethyl]cyclohexene Compound No. 30: 4-(trans-4-n-hexylcyclohexyl)-[2-(4-n-hexylphenyl)ethyl]cyclohexene The following compounds were obtained which were represented by the formula [Iaa] wherein $X_{11}$=alkoxy and Y=H.

Compound No. 31: 4-(trans-4-ethylcyclohexyl)-[2-(4-methoxyphenyl)ethyl]cyclohexene
m.p. 51° C. and clp. 114° C.

Compound No. 32: 4-(trans-4-n-propylcyclohexyl)-[2-(4-methoxyphenyl)ethyl]cyclohexene
m.p. 64° C. and clp. 139° C.

Compound No. 33: 4-(trans-4-n-butylcyclohexyl)-[2-(4-methoxyphenyl)ethyl]cyclohexene
m.p. 45° C. and clp 134° C.

Compound No. 34: 4-(trans-4-n-pentylcyclohexyl)-[2-(4-methoxyphenyl)ethyl]cyclohexene
m.p. 55° C. and clp. 142° C.

Compound No. 35: 4-(trans-4-n-hexylcyclohexyl)-[2-(4-methoxyphenyl)ethyl]cyclohexene Compound No. 36: 4-(trans-4-ethylcyclohexyl)-[2-(4-ethoxyphenyl)ethyl]cyclohexene Compound No. 37: 4-(trans-4-n-propylcyclohexyl)-[2-(4-ethoxyphenyl)ethyl]cyclohexene Compound No. 38: 4-(trans-4-n-butylcyclohexyl)-[2-(4-ethoxyphenyl)ethyl]cyclohexene Compound No. 39: 4-(trans-4-n-pentylcyclohexyl)-[2-(4-ethoxyphenyl)ethyl]cyclohexene Compound No. 40: 4-(trans-4-n-hexylcyclohexyl)-[2-(4-ethoxyphenyl)ethyl]cyclohexene Compound No. 41: 4-(trans-4-ethylcyclohexyl)-[2-(4-n-propoxyphenyl)ethyl]cyclohexene Compound No. 42: 4-(trans-4-n-propylcyclohexyl)-[2-(4-n-propoxyphenyl)ethyl]cyclohexene Compound No. 43: 4-(trans-4-n-butylcyclohexyl)-[2-(4-n-propoxyphenyl)ethyl]cyclohexene Compound No. 44: 4-(trans-4-n-pentylcyclohexyl)-[2-(4-n-propoxyphenyl)ethyl]cyclohexene Compound No. 45: 4-(trans-4-n-hexylcyclohexyl)-[2-(4-n-propoxyphenyl)ethyl]cyclohexene Compound No. 46: 4-(trans-4-ethylcyclohexyl)-[2-(4-n-butyloxyphenyl)ethyl] cyclohexene Compound No. 47: 4-(trans-4-n-propylcyclohexyl)-[2-(4-n-butyloxyphenyl)ethyl]cyclohexene Compound No. 48: 4-(trans-4-n-butylcyclohexyl)-[2-(4-n-butyloxyphenyl)ethyl]cyclohexene Compound No. 49: 4-(trans-4-n-pentylcyclohexyl)-[2-(4-n-butyloxyphenyl)ethyl]cyclohexene Compound No. 50: 4-(trans-4-n-hexylcyclohexyl)-[2-(4-n-butyloxyphenyl)ethyl]cyclohexene Compound No. 51: 4-(trans-4-ethylcyclohexyl)-[2-(4-n-pentyloxyphenyl)ethyl]cyclohexene Compound No. 52: 4-(trans-4-n-propylcyclohexyl)-[2-(4-n-pentyloxyphenyl)ethyl]cyclohexene Compound No. 53: 4-(trans-4-n-butylcyclohexyl)-[2-(4-n-pentyloxyphenyl)ethyl]cyclohexene Compound No. 54: 4-(trans-4-n-pentylcyclohexyl)-[2-(4-n-pentyloxyphenyl)ethyl]cyclohexene Compound No. 55: 4-(trans-4-n-hexylcyclohexyl)-[2-(4-n-pentyloxyphenyl)ethyl]cyclohexene Compound No. 56: 4-(trans-4- ethylcyclohexyl) -[2-(4-n-hexyloxyphenyl)ethyl]cyclohexene Compound No. 57: 4-(trans-4-n-propylcyclohexyl)-[2-(4-n-hexyloxyphenyl)ethyl]cyclohexene Compound No. 58: 4-(trans-4-n-butylcyclohexyl)-[2-(4-n-hexyloxyphenyl)ethyl]cyclohexene Compound No. 59: 4-(trans-4-n-pentylcyclohexyl)-[2-(4-n-hexyloxyphenyl)ethyl]cyclohexene Compound No. 60: 4-(trans-4-n-hexylcyclohexyl)-[2-(4-n-hexyloxyphenyl)ethyl]cyclohexene

EXAMPLE 3

Synthesis of 4-[2-(trans-4-n-propylcyclohexyl)ethyl]-[2-(4-ethylphenyl)ethyl]cyclohexene [Compound No. 61 (in the formula [Iab], $X_{11}$=ethyl and Y=H)]:

The same procedure as in Example 1 was effected except that 2-(4-methylphenyl)ethyl bromide used in Example 1 was replaced with 2-(4-ethylphenyl)ethyl bromide and 4-(trans-4-n-propylcyclohexyl)cyclohexanone was replaced with 4-[2-(trans-4-n-propylcyclohexyl)ethyl]cyclohexanone, in order to obtain the desired compound.
clp. 94° C.

EXAMPLE 4

The same procedure as in Example 1 was effected except that 2-(4-ethylphenyl)ethyl bromide used in Example 3 was replaced with a suitable phenethyl bromide derivative and 4-[2-(trans-4-n-propylcyclohexyl)ethyl]-cyclohexanone was replaced with a suitable ethylcyclohexanone derivative, in order to obtain the following compounds (in the formula [Iab], $X_{11}$=alkyl and Y=H).

Compound No. 62: 4-[2-(trans-4-ethylcyclohexyl)ethyl]-[2-(4-methylphenyl)ethyl]cyclohexene Compound No. 63: 4-[2-(trans-4-n-propylcyclohexyl)ethyl]-[2-(4-methylphenyl)ethyl]cyclohexene Compound No 64: 4-[2-(trans-4-n-butylcyclohexyl)ethyl]-[2-(4-methylphenyl)ethyl]cyclohexene Compound No. 65: 4-[2-(trans-4-n-pentylcyclohexyl)ethyl]-[2-(4-methylphenyl)ethyl]cyclohexene Compound No. 66: 4-[2-(trans-4-n-hexylcyclohexyl)ethyl]-[2-(4-methylphenyl)ethyl]cyclohexene Compound No. 67: 4-[2-(trans-4-ethylcyclohexyl)ethyl][2-(4-ethylphenyl)ethyl]cyclohexene Compound No. 68: 4-[2-(trans-4-n-butylcyclohexyl)ethyl]-[2-(4-ethylphenyl)ethyl]cyclohexene Compound No. 69: 4-[2-(trans-4-n-pentylcyclohexyl)ethyl]-[2-(4-ethylphenyl)ethyl]cyclohexene Compound No. 70: 4-[2-(trans-4-n-hexylcyclohexyl)ethyl][2-(4-ethylphenyl)ethyl]-cyclohexene Compound No. 71: 4-[2-(trans-4-ethylcyclohexyl)ethyl][2-(4-n-propylphenyl)ethyl]-cyclohexene Compound No. 72: 4-[2-(trans-4-n-propylcyclohexyl)ethyl]-[2-(4-n-propylphenyl)ethyl]cyclohexene Compound No. 73: 4-[2-(trans-4-n-butylcyclohexyl)ethyl]-[2-(4-n-propylphenyl)ethyl]cyclohexene Compound No. 74: 4-[2-(trans-4-n-pentylcyclohexyl)ethyl]-[2-(4-n-propylphenyl)ethyl]cyclohexene Compound No. 75: 4-[2-(trans-4-n-hexylcyclohexyl)ethyl]-[2-(4-n-propylphenyl)ethyl]cyclohexene Compound No. 76: 4-[2-(trans-4-ethylcyclohexyl)ethyl]-[2-(4-n-butylphenyl)ethyl]cyclohexene Compound No. 77: 4-[2-(trans-4-n-propylcyclohexyl)ethyl]-[2-(4-n-butylphenyl)ethyl]cyclohexene Compound No. 78: 4-[2-(trans-4-n-butylcyclohexyl)ethyl]-[2-(4-n-butylphenyl)ethyl]cyclohexene Compound No. 79: 4-[2-(trans-4-n-pentylcyclohexyl)ethyl]-[2-(4-n-butylphenyl)ethyl]cyclohexene Compound No. 80: 4-[2-(trans-4-n-hexylcyclohexyl)ethyl]-[2-(4-n-butylphenyl)ethyl]cyclohexene
Compound No. 81: 4-[2-(trans-4-ethylcyclohexyl)ethyl]-[2-(4-n-pentylphenyl)ethyl]cyclohexene
Compound No. 82: 4-[2-(trans-4-n-propylcyclohexyl)ethyl]-[2-(4-n-pentylphenyl)ethyl]cyclohexene
Compound No. 83: 4-[2-(trans-4-n-butylcyclohexyl)ethyl]-[2-(4-n-pentylphenyl)ethyl]cyclohexene
Compound No. 84: 4-[2-(trans-4-n-pentylcyclohexyl)ethyl]-[2-(4-n-pentylphenyl)ethyl]cyclohexene
Compound No. 85: 4-[2-(trans-4-n-hexylcyclohexyl)ethyl]-[2-(4-n-pentylphenyl)ethyl]cyclohexene
Compound No. 86: 4-[2-(trans-4-ethylcyclohexyl)ethyl]-[2-(4-n-hexylphenyl)ethyl]cyclohexene
Compound No. 87: 4-[2-(trans-4-n-propylcyclohexyl)ethyl] -[2-(4-n-hexylphenyl)ethyl]cyclohexene
Compound No. 88: 4-[2-(trans-4-n-butylcyclohexyl)ethyl]-[2-(4-n-hexylphenyl)ethyl]cyclohexene
Compound No. 89: 4-[2-(trans-4-n-pentylcyclohexyl)ethyl]-[2-(4-n-hexylphenyl)ethyl]cyclohexene
Compound No. 90: 4-[2-(trans-4-n-hexylcyclohexyl)ethyl]-[2-(4-n-hexylphenyl)ethyl]cyclohexene The following compounds were obtained which were represented by the formula [Iab] wherein $X_{11}$=alkoxy and $Y$=H.

Compound No. 91: 4-[2-(trans-4-ethylcyclohexyl)ethyl]-[2-(4-methoxyphenyl)ethyl]cyclohexene
Compound No. 92: 4-[2-(trans-4-n-propylcyclohexyl)ethyl]-[2-(4-methoxyphenyl)ethyl]cyclohexene
Compound No. 93: 4-[2-(trans-4-n-butylcyclohexyl)ethyl]-[2-(4-methoxyphenyl)ethyl]cyclohexene
Compound No. 94: 4-[2-(trans-4-n-pentylcyclohexyl)ethyl]-[2-(4-methoxyphenyl)ethyl]cyclohexene
Compound No. 95: 4-[2-(trans-4-n-hexylcyclohexyl)ethyl]-[2-(4-methoxyphenyl)ethyl]cyclohexene
Compound No. 96: 4-[2-(trans-4-ethylcyclohexyl)ethyl]-[2-(4-ethoxyphenyl)ethyl]cyclohexene
Compound No. 97: 4-[2-(trans-4-n-propylcyclohexyl)ethyl]-[2-(4-ethoxyphenyl)ethyl]cyclohexene
Compound No. 98: 4-[2-(trans-4-n-butylcyclohexyl)ethyl] -[2-(4-ethoxyphenyl)ethyloyclohexene
Compound No. 99: 4-[2-(trans-4-n-pentylcyclohexyl)ethyl]-[2-(4-ethoxyphenyl)ethyl]cyclohexene
Compound No. 100: 4-[2-(trans-4-n-hexylcyclohexyl)ethyl]-[2-(4-ethoxyphenyl)ethyl]cyclohexene
Compound No. 101: 4-[2-(trans-4-ethylcyclohexyl)ethyl]-[2-(4-n-propoxyphenyl)ethyl]cyclohexene
Compound No. 102: 4-[2-(trans-4-n-propylcyclohexyl)ethyl]-[2-(4-n-propoxyphenyl)ethyl]cyclohexene
Compound No. 103: 4-[2-(trans-4-n-butylcyclohexyl)ethyl]-[2-(4-n-propoxyphenyl)ethyl]cyclohexene
Compound No. 104: 4-[2-(trans-4-n-pentylcyclohexyl)ethyl]-[2-(4-n-propoxyphenyl)ethyl]cyclohexene
Compound No. 105: 4-[2-(trans-4-n-hexylcyclohexyl)ethyl]-[2-(4-n-propoxyphenyl)ethyl]cyclohexene
Compound No. 106: 4-[2-(trans-4-ethylcyclohexyl)ethyl]-[2-(4-n-butyloxyphenyl)ethyl]cyclohexene
Compound No. 107: 4-[2-(trans-4-n-propylcyclohexyl)ethyl]-[2-(4-n-butyloxyphenyl)ethyl]cyclohexene
Compound No. 108: 4-[2-(trans-4-n-butylcyclohexyl)ethyl]-[2-(4-n-butyloxyphenyl)ethyl]cyclohexene
Compound No. 109: 4-[2-(trans-4-n-pentylcyclohexyl)ethyl]-[2-(4-n-butyloxyphenyl)ethyl]cyclohexene
Compound No. 110: 4-[2-(trans-4-n-hexylcyclohexyl)ethyl]-[2-(4-n-butyloxyphenyl)ethyl]cyclohexene
Compound No. 111: 4-[2-(trans-4-ethylcyclohexyl)ethyl]-[2-(4-n-pentyloxyphenyl)ethyl]cyclohexene
Compound No. 112: 4-[2-(trans-4-n-propoylcyclohexyl)ethyl]-[2-(4-n-pentyloxyphenyl)ethyl]cyclohexene
Compound No. 113: 4-[2-(trans-4-n-butylcyclohexyl)ethyl]-[2-(4-n-pentyloxyphenyl)ethyl]cyclohexene
Compound No. 114: 4-[2-(trans-4-n-pentylcyclohexyl)ethyl]-[2-(4-n-pentyloxyphenyl)ethyl]cyclohexene
Compound No. 115: 4-[2-(trans-4-n-hexylcyclohexyl)ethyl]-[2-(4-n-pentyloxyphenyl)ethyl]cyclohexene
Compound No. 116: 4-[2-(trans-4-ethylcyclohexyl)ethyl]-[2-(4-n-hexyloxyphenyl)ethyl]cyclohexene
Compound No. 117: 4-[2-(trans-4-n-propylcyclohexyl)ethyl]-[2-(4-n-hexyloxyphenyl)ethyl]cyclohexene
Compound No. 118: 4-[2-(trans-4-n-butylcyclohexyl)ethyl]-[2-(4-n-hexyloxyphenyl)ethyl]cyclohexene
Compound No. 119: 4-[2-(trans-4-n-pentylcyclohexyl)ethyl]-[2-(4-n-hexyloxyphenyl)ethyl]cyclohexene
Compound No. 120: 4-[2-(trans-4-n-hexylcyclohexyl)ethyl]-[2-(4-n-hexyloxyphenyl)ethyl]cyclohexene

EXAMPLE 5

Synthesis of 4-(trans-4-n-propylcyclohexyl)-[2-(3-fluoro-4-n-propylphenyl)ethyl]cyclohexene [Compound No. 121 (in the formula [Iaa], $X_{11}$=propyl and $Y$=F]:

In a nitrogen gas stream, 30 ml of a THF solution containing 8.1 g of 2-(3-fluoro-4-n-propylphenyl)ethyl bromide was added dropwise at 20° C. into a three-necked flask in which 0.9 g of magnesium and 5 ml of THF were present. Afterward, the solution was stirred for 1 hour, and 20 ml of a THF solution containing 6.7 g of 4-(trans-4-n-propylcyclohexyl)cyclohexanone was then added dropwise thereto at 20° C. After stirring for 5 hours, the solution was cooled to 0° C., and 50 ml of 6 N hydrochloric acid and 50 ml of toluene were then added thereto. After the removal of a water layer, the solution was washed with 50 ml of a 1 N aqueous sodium hydroxide solution, and water washing was continued until the aqueous solution had become neutral. The resulting toluene solution was dried over anhydrous magnesium sulfate and then concentrated. Afterward, 0.3 g of p-toluenesulfonic acid and 20 ml of toluene were added thereto, followed by heating under reflux for 1 hour. At this time, a drainage pipe was used to remove water formed by azeotropy. The solution was then cooled to 20° C., and 50 ml of a 0.5 N aqueous sodium hydroxide solution and 50 ml of heptane were added thereto, followed by removing a water layer. Afterward, the solution was washed with 50 ml of a saturated sodium chloride solution three times, and then dried over anhydrous magnesium sulfate and concentrated. The thus treated solution was passed through an alumina-packed column by the use of a heptane solvent, followed by distillation, whereby 7.6 g of white crystals was obtained. The thus obtained crystals were further recrystallized from a hexane solvent and then dried in order to prepare 3.9 g of the desired compound. The chemical structure of the product was confirmed by NMR.

EXAMPLE 6

The same procedure as in Example 1 was effected except that 2-(3-fluoro-4-n-propylphenyl)ethyl bromide used in Example 5 was replaced with a suitable fluorophenethyl bromide derivative and 4-(trans-4-n-propylcyclohexyl)cyclohexanone was replaced with a suitable cyclohexanone derivative, thereby obtaining the following compounds (in the formula [Iaa], $X_{11}$=alkyl and $Y$=F).

Compound No. 122: 4-(trans-4-ethylcyclohexyl)-[2-(3-fluoro-4-methylphenyl)ethyl]cyclohexene
Compound No. 123: 4-(trans-4-n-propylcyclohexyl)-[2-(3-fluoro-4-methylphenyl)ethyl]cyclohexene
Compound No. 124: 4-(trans-4-n-butylcyclohexyl)-[2-(3-fluoro-4-methylphenyl)ethyl]cyclohexene
Compound No. 125: 4-(trans-4-n-pentylcyclohexyl)-[2-(3-fluoro-4-methylphenyl)ethyl]cyclohexene
Compound No. 126: 4-(trans 4-n-hexylcyclohexyl)-[2-(3-fluoro-4-methylphenyl)ethyl]cyclohexene
Compound No. 127: 4-(trans-4- ethylcyclohexyl) -[2-(3-fluoro-4-ethylphenyl)ethyl]cyclohexene
Compound No. 128: 4-(trans-4-n-propylcyclohexyl)-[2-(3-fluoro-4-ethylphenyl)ethyl]cyclohexene
Compound No. 129: 4-(trans-4-n-butylcyclohexyl)-[2-(3-fluoro-4-ethylphenyl)ethyl]cyclohexene
Compound No. 130: 4-(trans-4-n-pentylcyclohexyl)-[2-(3-fluoro-4-ethylphenyl)ethyl]cyclohexene
Compound No. 131: 4-(trans-4-n-hexylcyclohexyl)-[2-(3-fluoro-4-ethylphenyl)ethyl]cyclohexene
Compound No. 132: 4-(trans-4-ethylcyclohexyl)-[2-(3-fluoro-4-n-propylphenyl)ethyl]cyclohexene
Compound No. 133: 4-(trans-4-n-butylcyclohexyl)-[2-(3-fluoro-4-n-propylphenyl)ethyl]cyclohexene
Compound No. 134: 4-(trans-4-n-pentylcyclohexyl)-[2-(3-fluoro-4-n-propylphenyl)ethyl]cyclohexene
Compound No. 135: 4-(trans-4-n-hexylcyclohexyl)-[2-(3-fluoro-4-n-propylphenyl)ethyl]cyclohexene
Compound No. 136: 4-(trans-4-ethylcyclohexyl)-[2-(3-fluoro-4-n-butylphenyl)ethyl]cyclohexene
Compound No. 137: 4-(trans-4-n-propylcyclohexyl)-[2-(3-fluoro-4-n-butylphenyl)ethyl]cyclohexene
Compound No. 138: 4-(trans-4-n-butylcyclohexyl)-[2-(3-fluoro-4-n-butylphenyl)ethyl]cyclohexene
Compound No. 139: 4-(trans-4-n-pentylcyclohexyl)-[2-(3-fluoro- 4-n-butylphenyl)ethyl]cyclohexene
Compound No. 140: 4-(trans-4-n-hexylcyclohexyl)-[2-(3-fluoro-4-n-butylphenyl)ethyl]cyclohexene
Compound No. 141: 4-(trans-4-ethylcyclohexyl)-[2-(3-fluoro-4-n-pentylphenyl)ethyl]cyclohexene
Compound No. 142: 4-(trans-4-n-propylcyclohexyl)-[2-(3-fluoro-4-n-pentylphenyl)ethyl]cyclohexene
Compound No. 143: 4-(trans-4-n-butylcyclohexyl)-[2-(3-fluoro-4-n-pentylphenyl)ethyl]cyclohexene
Compound No. 144: 4-(trans-4-n-pentylcyclohexyl)-[2-(3-fluoro-4-n-pentylphenyl)ethyl]cyclohexene
Compound No. 145: 4-(trans-4-n-hexylcyclohexyl)-[2-(3-fluoro-4-n-pentylphenyl)ethyl]cyclohexene
Compound No. 146: 4-(trans-4-ethylcyclohexyl)-[2-(3-fluoro-4-n-hexylphenyl)ethyl]cyclohexene
Compound No. 147: 4-(trans-4-n-propylcyclohexyl)-[2-(3-fluoro-4-n-hexylphenyl)ethyl]cyclohexene
Compound No. 148: 4-(trans-4-n-butylcyclohexyl)-[2-(3-fluoro-4-n-hexylphenyl)ethyl]cyclohexene
Compound No. 149: 4-(trans-4-n-pentylcyclohexyl)-[2-(3-fluoro-4-n-hexylphenyl)ethyl]cyclohexene
Compound No. 150: 4-(trans-4-n-hexylcyclohexyl)-[2-(3-fluoro-4-n hexylphenyl)ethyl]cyclohexene The following compounds were obtained which are represented by the formula [Iaa] wherein $X_{11}$=alkoxy and Y=F.

Compound No. 151: 4-(trans-4-ethylcyclohexyl)-[2-(3-fluoro-4-methoxyphenyl)ethyl]cyclohexene
Compound No. 152: 4-(trans-4-n-propylcyclohexyl)-[2-(3-fluoro-4-methoxyphenyl)ethyl]cyclohexene
Compound No. 153: 4-(trans-4-n-butylcyclohexyl)-[2-(3-fluoro-4-methoxyphenyl)ethyl]cyclohexene
Compound No. 154: 4-(trans-4-n-pentylcyclohexyl)-[2-(3-fluoro-4-methoxyphenyl)ethyl]cyclohexene
Compound No. 155: 4-(trans-4-n-hexylcyclohexyl)-[2-(3-fluoro-4-methoxyphenyl)ethyl]cyclohexene
Compound No. 156: 4-(trans-4-ethylcyclohexyl)-[2-(3-fluoro-4-ethoxyphenyl)ethyl]cyclohexene
Compound No. 157: 4-(trans-4-n-propylcyclohexyl)-[2-(3-fluoro-4-ethoxyphenyl)ethyl]cyclohexene
Compound No. 158: 4-(trans-4-n-butylcyclohexyl)-[2-(3-fluoro-4-ethoxyphenyl)ethyl]cyclohexene
Compound No. 159: 4-(trans-4-n-pentylcyclohexyl)-[2-(3-fluoro-4-ethoxyphenyl)ethyl]cyclohexene
Compound No. 160: 4-(trans-4-n-hexylcyclohexyl)-[2-(3-fluoro-4-ethoxyphenyl)ethyl]cyclohexene
Compound No. 161: 4-(trans-4-ethylcyclohexyl)-[2-(3-fluoro-4-n-propoxyphenyl)ethyl]cyclohexene
Compound No. 162: 4-(trans-4-n-propylcyclohexyl)-[2-(3-fluoro-4-n-propoxyphenyl)ethyl]cyclohexene
Compound No. 163: 4-(trans-4-n-butylcyclohexyl)-[2-(3-fluoro-4-n-propoxyphenyl)ethyl]cyclohexene
Compound No. 164: 4-(trans-4-n-pentylcyclohexyl)-[2-(3-fluoro-4-n-propoxyphenyl)ethyl]cyclohexene
Compound No 165: 4-(trans-4-n-hexylcyclohexyl)-[2-(3-fluoro-4-n-propoxyphenyl)ethyl]cyclohexene
Compound No. 166: 4-(trans-4-ethylcyclohexyl)-[2-(3-fluoro-4-n-butyloxyphenyl)ethyl]cyclohexene
Compound No. 167: 4-(trans-4-n-propylcyclohexyl)-[2-(3-fluoro-4-n-butyloxyphenyl)ethyl]cyclohexene
Compound No. 168: 4-(trans-4-n-butylcyclohexyl)-[2-(3-fluoro-4-n-butyloxyphenyl)ethyl]cyclohexene
Compound No. 169: 4-(trans-4-n-pentylcyclohexyl)-[2-(3-fluoro-4-n-butyloxyphenyl)ethyl]cyclohexene
Compound No. 170: 4-(trans-4-n-hexylcyclohexyl)-[2-(3-fluoro-4-n-butyloxyphenyl)ethyl]cyclohexene
Compound No. 171: 4-(trans-4-ethylcyclohexyl)-[2-(3-fluoro-4-n-pentyloxyphenyl)ethyl]cyclohexene
Compound No. 172: 4-(trans-4-n-propylcyclohexyl)-[2-(3-fluoro-4-n-pentyloxyphenyl)ethyl]cyclohexene
Compound No. 173: 4-(trans-4-n-butylcyclohexyl)-[2-(3-fluoro-4-n-pentyloxyphenyl)ethyl]cyclohexene
Compound No. 174: 4-(trans-4-n-pentylcyclohexyl)-[2-(3-fluoro-4-n-pentyloxyphenyl)ethyl]cyclohexene
Compound No. 175: 4-(trans-4-n-hexylcyclohexyl)-[2-(3-fluoro-4-n-pentyloxyphenyl)ethyl]cyclohexene
Compound No. 176: 4-(trans-4-ethylcyclohexyl)-[2-(3-fluoro-4-n-hexyloxyphenyl)ethyl]cyclohexene
Compound No. 177: 4-(trans-4-n-propylcyclohexyl)-[2-(3-fluoro-4-n-hexyloxyphenyl)ethyl]cyclohexene
Compound No. 178: 4-(trans-4-n-butylcyclohexyl)-[2-(3-fluoro-4-n-hexyloxyphenyl)ethyl]cyclohexene
Compound No. 179: 4-(trans-4-n-pentylcyclohexyl)-[2-(3-fluoro-4-n-hexyloxyphenyl)ethyl]cyclohexene
Compound No. 180: 4-(trans-4-n-hexylcyclohexyl)-[2-(3-fluoro-4-n-hexyloxyphenyl)ethyl]cyclohexene

EXAMPLE 7

Synthesis of 4-[2-(trans-4-n-propylcyclohexyl)ethyl]-[2-(3-fluoro-4-n-propylphenyl)ethyl]cyclohexene [Compound No. 181 (in the formula [Iab], $X_{11}$=propyl and Y=F]:

The same procedure as in Example 1 was effected except that 4-(trans-4-n-propylcyclohexyl)cyclohexanone used in Example 5 was replaced with 4-[2-(trans-4-n-propylcyclohexyl)ethyl]cyclohexanone and then reacted with 2-(3-fluoro-4-n-propylphenyl)ethyl bromide, thereby obtaining the desired compound.

EXAMPLE 8

The same procedure as in Example 1 was effected except that 2-(3-fluoro-4-n-propylphenyl)ethyl bromide used in Example 7 was replaced with a suitable fluorophenethyl bromide derivative and 4-[2-(trans-4-n-propylcyclohexyl)ethyl]cyclohexanone was replaced with a suitable ethylcyclohexanone derivative, thereby obtaining the following compounds (in the formula [Iab], $X_{11}$=alkyl and Y=F).

Compound No. 182: 4-[2-(trans-4-ethylcyclohexyl)ethyl]-[2-(3-fluoro-4-methylphenyl)ethyl]cyclohexene Compound No. 183: 4-[2-(trans-4-n-propylcyclohexyl)ethyl]-[2-(3-fluoro-4-methylphenyl)ethyl]cyclohexene Compound No. 184: 4-[2-(trans-4-n-butylcyclohexyl)ethyl]-[2-(3-fluoro-4-methylphenyl)ethyl]cyclohexene Compound No. 185: 4-[2-(trans-4-n-pentylcyclohexyl)ethyl]-[2-(3-fluoro-4-methylphenyl)ethyl]cyclohexene Compound No. 186: 4-[2-(trans-4-n-hexylcyclohexyl)ethyl]-[2-(3-fluoro-4-methylphenyl)ethyl]cyclohexene Compound No. 187: 4-[2-(trans-4-ethylcyclohexyl)ethyl]-[2-(3-fluoro-4-ethylphenyl)ethyl]cyclohexene Compound No. 188: 4-[2-(trans-4-n-propylcyclohexyl)ethyl]-[2-(3-fluoro-4-ethylphenyl)ethyl]cyclohexene Compound No. 189: 4-[2-(trans-4-n-butylcyclohexyl)ethyl]-[2-(3-fluoro-4-ethylphenyl)ethyl]cyclohexene Compound No. 190: 4-[2-(trans-4-n-pentylcyclohexyl)ethyl]-[2-(3-fluoro-4-ethylphenyl)ethyl]cyclohexene Compound No. 191: 4-[2-(trans-4-n-hexylcyclohexyl)ethyl] -[2-(3-fluoro-4-ethylphenyl)ethyl]cyclohexene Compound No. 192: 4-[2-(trans-4-ethylcyclohexyl)ethyl]-[2-(3-fluoro-4-n-propylphenyl)ethyl]cyclohexene Compound No. 193: 4-[2-(trans-4-n-butylcyclohexyl)ethyl]-[2-(3-fluoro-4-n-propylphenyl)ethyl]cyclohexene Compound No. 194: 4-[2-(trans-4-n-pentylcyclohexyl)ethyl]-[2-(3-fluoro-4-n-propylphenyl)ethyl]cyclohexene Compound No. 195: 4-[2-(trans-4-n-hexylcyclohexyl)ethyl]-[2-(3-fluoro-4-n-propylphenyl)ethyl]cyclohexene Compound No. 196: 4-[2-(trans-4-ethylcyclohexyl)ethyl]-[2-(3-fluoro-4-n-butylphenyl)ethyl]cyclohexene Compound No. 197: 4-[2-(trans-4-n-propylcyclohexyl)ethyl]-[2-(3-fluoro-4-n-butylphenyl)ethyl]cyclohexene Compound No. 198: 4-[2-(trans-4-n-butylcyclohexyl)ethyl]-[2-(3-fluoro-4-n-butylphenyl)ethyl]cyclohexene Compound No. 199: 4-[2-(trans-4-n-pentylcyclohexyl)ethyl]-[2-(3-fluoro-4-n-butylphenyl)ethyl]cyclohexene Compound No. 200: 4-[2-(trans-4-n-hexylcyclohexyl)ethyl]-[2-(3-fluoro-4-n-butylphenyl)ethyl]cyclohexene Compound No. 201: 4-[2-(trans-4-ethylcyclohexyl)ethyl]-[2-(3-fluoro-4-n-pentylphenyl)ethyl]cyclohexene Compound No. 202: 4-[2-(trans-n-propylcyclohexyl)ethyl]-[2-(3-fluoro-4-n-pentylphenyl)ethyl]cyclohexene Compound No. 203: 4-[2-(trans-n-butylcyclohexyl)ethyl ]-[2-(3-fluoro-4-n-pentylphenyl)ethyl]cyclohexene Compound No. 204: 4-[2-(trans-n-pentylcyclohexyl)ethyl]-[2-(3-fluoro-4-n-pentylphenyl)ethyl]cyclohexene Compound No. 205: 4-[2-(trans-n-hexylcyclohexyl)ethyl]-[2-(3-fluoro-4-n-pentylphenyl)ethyl]cyclohexene Compound No. 206: 4-[2-(trans-4-ethylcyclohexyl)ethyl]-[2-(3-fluoro-4-n-hexylphenyl)ethyl]cyclohexene Compound No. 207: 4-[2-(trans-4-n-propylcyclohexyl)ethyl]-[2-(3-fluoro-4-n-hexylphenyl)ethyl]cyclohexene Compound No. 208: 4-[2-(trans-4-n-butylcyclohexyl)ethyl]-[2-(3-fluoro-4-n-hexylphenyl)ethyl]cyclohexene Compound No. 209: 4-[2-(trans-4-n-pentylcyclohexyl)ethyl]-[2-(3-fluoro-4-n-hexylphenyl)ethyl]cyclohexene Compound No. 210: 4-[2-(trans-4-n-hexylcyclohexyl)ethyl]-[2-(3-fluoro-4-n-hexylphenyl)ethyl]cyclohexene The following compounds were obtained which were represented by the formula [Iab] wherein $X_{11}$=alkoxy and Y=F.

Compound No. 211: 4-[2-(trans-4-ethylcyclohexyl)ethyl]-[2-(3-fluoro-4-methoxyphenyl)ethyl]cyclohexene Compound No. 212: 4-[2-(trans-4-n-propylcyclohexyl)ethyl]-[2-(3-fluoro-4-methoxyphenyl)ethyl]cyclohexene Compound No. 213: 4-[2-(trans-4-n-butylcyclohexyl)ethyl]-[2-(3-fluoro-4-methoxyphenyl)ethyl]cyclohexene Compound No. 214: 4-[2-(trans-4-n-pentylcyclohexyl)ethyl]-[2-(3-fluoro-4-methoxyphenyl)ethyl]cyclohexene Compound No. 215: 4-[2-(trans-4-n-hexylcyclohexyl)ethyl]-[2-(3-fluoro-4-methoxyphenyl)ethyl]cyclohexene Compound No. 216: 4-[2-(trans-4-ethylcyclohexyl)ethyl]-[2-(3-fluoro-4-ethoxyphenyl)ethyl]cyclohexene Compound No. 217: 4-[2-(trans-4-n-propylcyclohexyl)ethyl]-[2-(3-fluoro-4-ethoxyphenyl)ethyl]cyclohexene Compound No. 218: 4-[2-(trans-4-n-butylcyclohexyl)ethyl]-[2-(3-fluoro-4-ethoxyphenyl)ethyl]cyclohexene Compound No. 219: 4-[2-(trans-4-n-pentylcyclohexyl)ethyl]-[2-(3-fluoro-4-ethoxyphenyl)ethyl]cyclohexene Compound No. 220: 4-[2-(trans-4-n-hexylcyclohexyl)ethyl]-[2-(3-fluoro-4-ethoxyphenyl)ethyl]cyclohexene Compound No. 221: 4-[2-(trans-4-ethylcyclohexyl)ethyl]-[2-(3-fluoro-4-n-propoxyphenyl)ethyl]cyclohexene Compound No. 222: 4-[2-(trans-4-n-propylcyclohexyl)ethyl]-[2-(3-fluoro-4-n-propoxyphenyl)ethyl]cyclohexene Compound No. 223: 4-[2-(trans-4-n-butylcyclohexyl)ethyl]-[2-(3-fluoro-4-n-propoxyphenyl)ethyl]cyclohexene Compound No. 224: 4-[2-(trans-4-n-pentylcyclohexyl)ethyl]-[2-(3-fluoro-4-n-propoxyphenyl)ethyl]cyclohexene Compound No. 225: 4-[2-(trans-4-n-hexylcyclohexyl)ethyl]-[2-(3-fluoro-4-n-propoxyphenyl)ethyl]cyclohexene Compound No. 226: 4-[2-(trans-4-ethylcyclohexyl)ethyl] -[2-(3-fluoro-4-n-butyloxyphenyl)ethyl]cyclohexene Compound No. 227: 4-[2-(trans-4-n-propylcyclohexyl)ethyl]-[2-(3-fluoro-4-n-butyloxyphenyl)ethyl]cyclohexene Compound No. 228: 4-[2-(trans-4-n-butylcyclohexyl)ethyl]-[2-(3-fluoro-4-n-butyloxyphenyl)ethyl]cyclohexene Compound No. 229: 4-[2-(trans-4-n-pentylcyclohexyl)ethyl]-[2-(3-fluoro-4-n-butyloxyphenyl)ethyl]cyclohexene Compound No. 230: 4-[2-(trans-4-n-hexylcyclohexyl)ethyl]-[2-(3-fluoro-4-n-butyloxyphenyl)ethyl]cyclohexene Compound No. 231: 4-[2-(trans-4-ethylcyclohexyl)ethyl]-[2-(3-fluoro-4-n-pentyloxyphenyl)ethyl]cyclohexene Compound No. 232: 4-[2-(trans-4-n-propylcyclohexyl)ethyl]-[2-(3-fluoro-4-n-pentyloxyphenyl)ethyl]cyclohexene Compound No. 233: 4-[2-(trans-4-n-butylcyclohexyl)ethyl]-[2-(3-fluoro-4-n-pentyloxyphenyl)ethyl]cyclohexene Compound No. 234: 4-[2-(trans-4-n-pentylcyclohexyl)ethyl]-[2-(3 fluoro-4-n-pentyloxyphenyl)ethyl]cyclohexene Compound No. 235: 4-[2-(trans-4-n-hexylcyclohexyl)ethyl]-[2-(3-fluoro-4-n-pentyloxyphenyl)ethyl]cyclohexene Compound No. 236: 4-[2-(trans-4-ethylcyclohexyl)ethyl]-[2-(3-fluoro-4-n-hexyloxyphenyl)ethyl]cyclohexene Compound No. 237: 4-[2-(trans-4-n-propylcyclohexyl)ethyl]-[2-(3-fluoro-4-n-hexyloxyphenyl)ethyl]cyclohexene Compound No. 238: 4-[2-(trans-4-n-butylcyclohexyl)ethyl]-[2-(3-fluoro-4-n-hexyloxyphenyl)ethyl]cyclohexene Compound No. 239: 4-[2-(trans-4-n-pentylcyclohexyl)ethyl]-[2-(3-fluoro-4-n-hexyloxyphenyl)ethyl]cyclohexene Compound No. 240: 4-[2-(trans-4-n-hexylcyclohexyl)ethyl]-[2-(3-fluoro-4-n-hexyloxyphenyl)ethyl]cyclohexene

EXAMPLE 9

Synthesis of 4-(trans-4-n-propylcyclohexyl)-[2-(4-fluorophenyl)ethyl]cyclohexene [Compound No. 241 (in the formula [Iac], Y=H and R=propyl):

The same procedure as in Example 1 was effected except that 2-(4-methylphenyl)ethyl bromide used in Example 1 was replaced with 2-(4-fluorophenyl)ethyl bromide and then reacted with 4-(trans-4-n-propylcyclohexyl)cyclohexanone, in order to obtain the desired compound.

m.p. 25° C. and clp. 95° C.

EXAMPLE 10

The same procedure as in Example 1 was effected except that 2-(4-fluorophenyl)ethyl bromide used in Example 9 was replaced with a suitable fluorophenylethyl bromide derivative and 4-(trans-4-n-propylcyclohexyl)cyclohexanone was replaced with a suitable cyclohexanone derivative, in order to obtain the following compounds (in the formula [Iac], Y=H).

Compound No. 242: 4-(trans-4-methylcyclohexyl)-[2-(4fluorophenyl)ethyl]cyclohexene Compound No. 243: 4-(trans-4-ethylcyclohexyl)-[2-(4-fluorophenyl)ethyl]cyclohexene Compound No. 244: 4-(trans-4-n-butylcyclohexyl)-[2-(4-fluorophenyl)ethyl]cyclohexene Compound No. 245: 4-(trans-4-n-pentylcyclohexyl)-[2-(4-fluorophenyl)ethyl]cyclohexene
m.p. 17° C. and clp. 99° C.

Compound No. 246: 4-(trans-4-n-hexylcyclohexyl)-[2-(4-fluorophenyl)ethyl]cyclohexene Compound No. 247: 4-(trans-4-n-heptylcyclohexyl)-[2-(4-fluorophenyl)ethyl]cyclohexene
clp. 100° C.

Compound No. 248: 4-(trans-4-n-octylcyclohexyl)-[2-(4-fluorophenyl)ethyl]cyclohexene Compound No. 249: 4-(trans-4-n-nonylcyclohexyl)-[2-(4-fluorophenyl)ethyl]cyclohexene Compound No. 250: 4-(trans-4-n-decylcyclohexyl)-[2-(4-fluorophenyl)ethyl]cyclohexene The following compounds were obtained which were represented by the formula [Iac] wherein Y=F.

Compound No. 251: 4-(trans-4-methylcyclohexyl)-[2-(3,4-difluorophenyl)ethyl]cyclohexene Compound No. 252: 4-(trans-4-ethylcyclohexyl)-[2-(3,4-difluorophenyl)ethyl]cyclohexene
m.p. 26° C. and clp. 43° C.

Compound No. 253: 4-(trans-4-n-propylcyclohexyl)-[2-(3,4-difluorophenyl)ethyl]cyclohexene
m.p. 9° C. and clp. 71° C.

Compound No. 254: 4-(trans-4-n-butylcyclohexyl)-[2-(3,4-difluorophenyl)ethyl]cyclohexene Compound No. 255: 4-(trans-4-n-pentylcyclohexyl)-[2-(3,4-difluorophenyl)ethyl]cyclohexene
m.p. 13° C. and clp. 81° C.

Compound No. 256: 4-(trans-4-n-hexylcyclohexyl)-[2-(3,4-difluorophenyl)ethyl]cyclohexene Compound No. 257: 4-(trans-4-n-heptylcyclohexyl)-[2-(3,4-difluorophenyl)ethyl]cyclohexene Compound No. 258: 4-(trans-4-n-octylcyclohexyl)-[2-(3,4-difluorophenyl)ethyl]cyclohexene Compound No. 259: 4-(trans-4-n-nonylcyclohexyl)-[2-(3,4-difluorophenyl)ethyl]cyclohexene Compound No. 260: 4-(trans-4-n-decylcyclohexyl)-[2-(3,4-difluorophenyl)ethyl]cyclohexene

EXAMPLE 11

Synthesis of 4-[2-(trans-4-n-propylcyclohexyl)ethyl]-[2-(4-fluorophenyl)ethyl]cyclohexene [Compound No. 261 (in the formula [Iad], Y=H and R=n-propyl):

The same procedure as in Example 1 was effected except that 4-(trans-4-n-propylcyclohexyl)cyclohexanone used in Example 9 was replaced with 4-[2-(trans-4-n-propylcyclohexyl)ethyl] cyclohexanone and then reacted with 2-(4-fluorophenyl)ethyl bromide, in order to obtain the desired compound.

EXAMPLE 12

The same procedure as in Example 1 was effected except that 4-[2-(trans-4-n-propylcyclohexyl)ethyl]cyclohexanone used in Example 11 was replaced with a suitable ethylcyclohexanone derivative and then reacted with 2-(4-fluorophenyl)ethyl bromide, in order to obtain the following compounds (in the formula [Iad], Y=H).

Compound No. 262: 4-[2-(trans-4-methylcyclohexyl)ethyl]-[2-(4-fluorophenyl)ethyl]cyclohexene Compound No. 263: 4-[2-(trans-4-ethylcyclohexyl)ethyl]-[2-(4-fluorophenyl)ethyl]cyclohexene Compound No. 264: 4-[2-(trans-4-n-butylcyclohexyl)ethyl]-[2-(4-fluorophenyl)ethyl]cyclohexene Compound No. 265: 4-[2-(trans-4-n-pentylcyclohexyl)ethyl]-[2-(4-fluorophenyl)ethyl]cyclohexene Compound No. 266: 4-[2-(trans-4-n-hexylcyclohexyl)ethyl]-[2-(4-fluorophenyl)ethyl]cyclohexene Compound No. 267: 4-[2-(trans-4-n-heptylcyclohexyl)ethyl]-[2-(4-fluorophenyl)ethyl]cyclohexene Compound No. 268: 4-[2-(trans-4-n-octylcyclohexyl)ethyl]-[2-(4-fluorophenyl)ethyl]cyclohexene Compound No. 269: 4-[2-(trans-4-n-nonylcyclohexyl)ethyl] -[2-(4-fluorophenyl)ethyl]cyclohexene Compound No. 270: 4-[2-(trans-4-n-decylcyclohexyl)ethyl]-[2-(4-fluorophenyl)ethyl]cyclohexene The following compounds were obtained which were represented by the formula [Iad] wherein Y=F.

Compound No. 271: 4-[2-(trans-4-methylcyclohexyl)ethyl]-[2-(3,4-difluorophenyl)ethyl]cyclohexene Compound No. 272: 4-[2-(trans-4-ethylcyclohexyl)ethyl]-[2-(3,4-difluorophenyl)ethyl]cyclohexene Compound No. 273: 4-[2-(trans-4-n-propylcyclohexyl)ethyl]-[2-(3,4-difluorophenyl)ethyl]cyclohexene m.p. 30.5° C. and clp. 61.1° C.

Compound No. 274: 4-[2-(trans-4-n-butylcyclohexyl)ethyl]-[2-(3,4-difluorophenyl)ethyl]cyclohexene Compound No. 275: 4-[2-(trans-4-n-pentylcyclohexyl)ethyl]-[2-(3,4-difluorophenyl)ethyl]cyclohexene Compound No. 276: 4-[2-(trans-4-n-hexylcyclohexyl)ethyl]-[2-(3,4-difluorophenyl)ethyl]cyclohexene Compound No. 277: 4-[2-(trans-4-n-heptylcyclohexyl)ethyl]-[2-(3,4-difluorophenyl)ethyl]cyclohexene Compound No. 278: 4-[2-(trans-4-n-octylcyclohexyl)ethyl]-[2-(3,4-difluorophenyl)ethyl]cyclohexene Compound No. 279: 4-[2-(trans-4-n-nonylcyclohexyl)ethyl]-[2-(3,4-difluorophenyl)ethyl]cyclohexene Compound No. 280: 4-[2-(trans-4-decylcyclohexyl)ethyl] -[2-(3,4-difluorophenyl)ethyl]cyclohexene

EXAMPLE 13

Synthesis of 4-n-propyl-[2-(4-methoxyphenyl)ethyl]-cyclohexene [Compound No. 281 (in the formula [Iac], $X_{11}$=CH$_3$O and R=n-C$_3$H$_7$]:

The same procedure as in Example 1 was effected except that 2-(4-methylphenyl)ethyl bromide used in Example 1 was replaced with 2-(4-methoxyphenyl)ethyl bromide and 4-(trans-4-n-propylcyclohexyl)cyclohexanone was replaced with 4-n-propylcyclohexanone, in order to obtain the desired compound.

EXAMPLE 14

The same procedure as in Example 1 was effected except that 2-(4-methylphenyl)ethyl bromide used in Example 1 was replaced with a suitable phenethyl bromide derivative and 4-(trans-4-n-propylcyclohexyl)cyclohexanone was replaced with a suitable cyclohexanone derivative, in order to obtain the following compounds (in the formula [Iae], $X_{11}$=alkoxy).

Compound No. 282: 4-ethyl-[2-(4-methoxyphenyl)ethyl]cyclohexene

Compound No. 283: 4-n-buthyl-[2-(4-methoxyphenyl)ethyl]cyclohexene

Compound No. 284: 4-n-pentyl-[2-(4-methoxyphenyl)ethyl]cyclohexene

Compound No. 285: 4-n-hexyl-[2-(4-methoxyphenyl)ethyl]cyclohexene

Compound No. 286: 4-n-heptyl-[2-(4-methoxyphenyl)ethyl]cyclohexene

Compound No. 287: 4-n-octyl-[2-(4-methoxyphenyl)ethyl]cyclohexene

Compound No. 288: 4-n-nonyl-[2-(4-methoxyphenyl)ethyl]cyclohexene

Compound No. 289: 4-n-decyl-[2-(4-methoxyphenyl)ethyl]cyclohexene

Compound No. 290: 4-ethyl-[2-(4-ethoxyphenyl)ethyl]-cyclohexene

Compound No. 291: 4-n-propyl-[2-(4-ethoxyphenyl)ethyl]cyclohexene

Compound No. 292: 4-n-butyl-[2-(4-ethoxyphenyl)ethyl]cyclohexene

Compound No. 293: 4-n-pentyl-[2-(4-ethoxyphenyl)ethyl]cyclohexene

Compound No. 294: 4-n-hexyl-[2-(4-ethoxyphenyl)ethyl]cyclohexene

Compound No. 295: 4-n-heptyl-[2-(4-ethoxyphenyl)ethyl]cyclohexene

Compound No. 296: 4-n-octyl-[2-(4-ethoxyphenyl)ethyl]cyclohexene

Compound No. 297: 4-n-nonyl-[2-(4-ethoxyphenyl)ethyl]cyclohexene

Compound No. 298: 4-n-decyl-[2-(4-ethoxyphenyl)ethyl]cyclohexene

Compound No. 299: 4-ethyl-[2-(4-n-propoxyphenyl)ethyl]cyclohexene

Compound No. 300: 4-n-propyl-[2-(4-n-propoxyphenyl)ethyl]cyclohexene

Compound No. 301: 4-n-butyl-[2-(4-n-propoxyphenyl)ethyl]cyclohexene

Compound No. 302: 4-n-pentyl-[2-(4-n-propoxyphenyl)ethyl]cyclohexene

Compound No. 303: 4-n-hexyl-[2-(4-n-propoxyphenyl)ethyl]cyclohexene

Compound No. 304: 4-n-heptyl-[2-(4-n-propoxyphenyl)ethyl]cyclohexene

Compound No. 305: 4-n-octyl-[2-(4-n-propoxyphenyl)ethyl]cyclohexene

Compound No. 306: 4-n-nonyl-[2-(4-n-propoxyphenyl)ethyl]cyclohexene

Compound No. 307: 4-n-decyl-[2-(4-n-propoxyphenyl)ethyl]cyclohexene

Compound No. 308: 4-ethyl-[2-(4-n-butyloxyphenyl)ethyl]cyclohexene

Compound No. 309: 4-n-propyl-[2-(4-n-butyloxyphenyl)ethyl]cyclohexene

Compound No. 310: 4-n-butyl-[2-(4-n-butyloxyphenyl)ethyl]cyclohexene

Compound No. 311: 4-n-pentyl-[2-(4-n-butyloxyphenyl)ethyl]cyclohexene

Compound No. 312: 4-n-hexyl-[2-(4-n-butyloxyphenyl)ethyl]cyclohexene

Compound No. 313: 4-n-heptyl-[2-(4-n-butyloxyphenyl)ethyl]cyclohexene

Compound No. 314: 4-n-octyl-[2-(4-n-butyloxyphenyl)ethyl]cyclohexene

Compound No. 315: 4-n-nonyl-[2-(4-n-butyloxyphenyl)ethyl]cyclohexene

Compound No. 316: 4-n-decyl-[2-(4-n-butyloxyphenyl)ethyl]cyclohexene

Compound No. 317: 4-ethyl-[2-(4-n-pentyloxyphenyl)ethyl]cyclohexene

Compound No. 318: 4-n-propyl-[2-(4-n-pentyloxyphenyl)ethyl]cyclohexene

Compound No. 319: 4-n-butyl-[2-(4-n-pentyloxyphenyl)ethyl]cyclohexene

Compound No. 320: 4-n-pentyl-[2-(4-n-pentyloxyphenyl)ethyl]cyclohexene

Compound No. 321: 4-n-hexyl-[2-(4-n-pentyloxyphenyl)ethyl]cyclohexene

Compound No. 322: 4-n-heptyl-[2-(4-n-pentyloxyphenyl)ethyl] cyclohexene

Compound No. 323: 4-n-octyl-[2-(4-n-pentyloxyphenyl)ethyl]cyclohexene

Compound No 324: 4-n-nonyl-[2-(4-n-pentyloxyphenyl)ethyl]cyclohexene

Compound No. 325: 4-n-decyl-[2-(4-n-pentyloxyphenyl)ethyl]cyclohexene

EXAMPLE 15

Synthesis of 4-n-propyl-[2-(4-fluorophenyl)ethyl]cyclohexene [Compound No. 326 (in the formula [Iaf], Y=H and R=n-C₃H₇):

The same procedure as in Example 1 was effected except that 2-(4-methylphenyl)ethyl bromide used in Example 1 was replaced with 2-(4-fluorophenyl)ethyl bromide and 4-(trans-4-n-propylcyclohexyl)cyclohexanone was replaced with 4-n-propylcyclohexanone, in order to obtain the desired compound.

EXAMPLE 16

The same procedure as in Example 1 was effected except that 2-(4-methylphenyl)ethyl bromide used in Example 1 was replaced with 2-(4-fluorophenyl)ethyl bromide derivative and 4-(trans-4-n-propylcyclohexyl)cyclohexanone was replaced with a suitable cyclohexanone derivative, in order to obtain the following compounds (in the formula [Iaf], Y=H).

Compound No. 327: 4-ethyl-[2-(4-fluorophenyl)ethyl]cyclohexene
Compound No. 328: 4-n-butyl-[2-(4-fluorophenyl)ethyl]cyclohexene
Compound No. 329: 4-n-pentyl-[2-(4-fluorophenyl)ethyl]cyclohexene
Compound No. 330: 4-n-hexyl-[2-(4-fluorophenyl)ethyl]cyclohexene
Compound No. 331: 4-n-heptyl-[2-(4-fluorophenyl)ethyl]cyclohexene
Compound No. 332: 4-n-octyl-[2-(4-fluorophenyl)ethyl]cyclohexene
Compound No. 333: 4-n-nonyl-[2-(4-fluorophenyl)ethyl]cyclohexene
Compound No. 334: 4-n-decyl-[2-(4-fluorophenyl)ethyl]cyclohexene

EXAMPLE 17

Synthesis of 4-n-propyl-[2-(3,4-difluorophenyl)ethyl]cyclohexene [Compound No. 335 (in the formula [Iaf], Y=F):

The same procedure as in Example 1 was effected except that 2-(4-methylphenyl)ethyl bromide used in Example 1 was replaced with 2-(3,4-difluorophenyl)ethyl bromide and 4-(trans-4-n-propylcyclohexyl)cyclohexanone was replaced with 4-n-propylcyclohexanone, in order to obtain the desired compound.

m.p. 3° C. and(clp. −35° C.

EXAMPLE 18

The same procedure as in Example 1 was effected except that 2-(4-methylphenyl)ethyl bromide used in Example 1 was replaced with a 2-(3,4-difluorophenyl)ethyl bromide derivative and 4-(trans-4 -n-propylcyclohexyl)cyclohexanone was replaced with a suitable cyclohexanone derivative, in order to obtain the following compounds (in the formula [Iaf], Y=F).

Compound No. 336: 4-ethyl-[2-(3,4-difluorophenyl)ethyl]cyclohexene
Compound No. 337: 4-n-butyl-[2-(3,4-difluorophenyl)ethyl]cyclohexene
Compound No. 338: 4-n-pentyl-[2-(3,4-difluorophenyl)ethyl]cyclohexene
Compound No. 339: 4-n-hexyl-[2-(3,4-difluorophenyl)ethyl]cyclohexene
Compound No. 340: 4-n-heptyl-[2-(3,4-difluorophenyl)ethyl]cyclohexene
Compound No. 341: 4-n-octyl-[2-(3,4-difluorophenyl)ethyl]cyclohexene
Compound No. 342: 4-n-nonyl-[2-(3,4-difluorophenyl)ethyl]cyclohexene
Compound No. 343: 4-n-decyl-[2-(3,4-difluorophenyl)ethyl] cyclohexene

EXAMPLE 19

Synthesis of 4-(trans-4-n-pentylcyclohexyl)-1-[2-(4-cyanophenyl)ethyl]cyclohexene [Compound No. 344 (in the formula [Iba], Y=H and R=C₅H₁₁]:

(i) Synthesis of 4-(trans-4-n-pentylcyclohexyl)cyclohexylidene-2-(4-bromophenyl)ethane:

At a temperature of −50° C., 5.6 g of potassium tert-butoxide was added into a 500-ml three-necked flask in which 26.3 g of 2-(4-bromophenyl)ethyltriphenylphosphonium bromide and 100 ml of THF were present. The resulting solution was then stirred at −50° C. for 1 hour, and 50 ml of a THF solution containing 10.0 g of 4-(trans-4-n-pentylcyclohexyl)cyclohexanone was added dropwise to the solution. Afterward, the solution was stirred for 10 hours, raising its temperature to room temperature gradually. To the solution was added 300 ml of water, followed by stirring, and extraction was then carried out with 200 ml of toluene. The resulting organic layer was washed with 300 ml of water twice, and then dried over anhydrous magnesium sulfate and concentrated. To the thus concentrated solution was then added 300 ml of heptane to deposit crystals, and the latter were removed therefrom by filtration. The filtrate was passed through a column packed with silica gel and then concentrated. Next, the solution was recrystallized from a mixed solvent of an alcohol and ethyl acetate and then dried in order to obtain 10.1 g of the desired compound.

m.p. 73° C.

(ii) Synthesis of 4-(trans-4-n-pentylcyclohexyl)-1-[2-(4-bromophenyl)ethyl]cyclohexene:

To a three-necked flask in which 6.6 g of metachloroperbenzoic acid, 5.3 g of potassium carbonate and 70 ml of chloroform were present was added dropwise 30 ml of a chloroform solution containing 8.0 g of the compound obtained in the above-mentioned process (i) at 10° C. The solution was stirred for 3 hours, and insoluble matters were then removed therefrom by filtration. Afterward, 50 ml of an aqueous sodium thiosulfate solution was added to the solution. After the removal of a water layer, the solution was then washed with 50 ml of a 1 N aqueous sodium hydroxide solution, and water washing was continued until the wash liquid became neutral. The solution was then dried over anhydrous magnesium sulfate and then concentrated, thereby obtaining 8.9 g of an oily material.

Afterward, 30 ml of a THF solution containing the thus obtained material was added dropwise at 20° C. to a 200-ml three necked flask in which 29 ml of a 1 mol solution of lithium hydride triethylboron was present. After stirring for one day, 100 ml of water and 100 ml of toluene were added thereto, and a water layer was then removed therefrom. The resulting organic layer was washed with 100 mol of water twice, and it was then dried over anhydrous magnesium sulfate and concentrated.

To the concentrated solution were added 0.1 g of paratoluenesulfonic acid monohydrate and 50 ml of toluene, followed by heating under reflux for 1 hour. At this time, a drainage pipe was used to remove water formed by azeotropy. After cooling, 50 ml of a 0.5 N aqueous sodium hydroxide solution and 50 ml of heptane were added to the solution, followed by removing a water layer. Afterward, the solution was washed with 50 ml of a saturated sodium chloride solution three times, and it was then dried over anhydrous magnesium sulfate and concentrated. The thus treated solution was passed through a silica gel-packed column by the use of a heptane solvent, and the used heptane was then distilled off, whereby 5.6 g of white crystals was obtained. The thus obtained crystals were further recrystallized from a mixed solvent of an alcohol and heptane, and then dried in order to prepare 3.5 g of the desired compound. The structure of the product was confirmed by NMR.

m.p. 58° C. and clp. 121° C.

(iii) Synthesis of 4-(trans-4-n-pentylcyclohexyl)- 1-(2-(4-cyanophenyl)ethyl)cyclohexene:

In a 100-ml three-necked flask were placed 3.5 g of the compound obtained in the above-mentioned process (ii), 0.9 g of copper cyanide (I) and 30 ml of DMF, followed by heating under reflux for 24 hours. After standing, 20 ml of aqueous ammonia and 50 ml of toluene were added to the solution, and a water layer was then removed therefrom. The organic layer was then filtered to remove insoluble matters therefrom. The resulting filtrate was washed with 50 ml of 2 N hydrochloric acid and then 50 ml of an aqueous saturated sodium hydrogencarbonate solution in this order, and it was further washed with water until the wash liquid became neutral. Afterward, the solution was dried over anhydrous magnesium sulfate, and the used solvent was then distilled off. The residue was passed through a silica gel column by the use of a mixed solvent of heptane and toluene(1:1). After concentration, the solution was recrystallized from a heptane solvent and then dried, thereby obtaining 1.5 g of the desired compound. The structure of the product was confirmed by NMR.

m.p. 70° C. and clp. 148° C.

EXAMPLE 20

The same procedure as in Example 19 was effected except that 4-(trans-4-n-pentylcyclohexyl)cyclohexanone used in Example 19-(i) was replaced with a suitable cyclohexanone derivative, in order to obtain the following compounds (in the formula [Iba], Y=H).

Compound No. 345: 4-(trans-4-ethylcyclohexyl)-1-[2-(4-cyanophenylethyl)cyclohexene
Compound No. 346: 4-(trans-4-n-propylcyclohexyl)-1-[2-(4-cyanophenyl)ethyl]cyclohexene
Compound No. 347: 4-(trans-4-n-butylcyclohexyl)-1-[2-(4-cyanophenyl)ethyl]cyclohexene
Compound No. 348: 4-(trans-4-n-hexylcyclohexyl)-1-[2-(4-cyanophenyl)ethyl]cyclohexene
Compound No. 349: 4-(trans-4-n-heptylcyclohexyl)-1-[2-(4-cyanophenyl)ethyl]cyclohexene
Compound No. 350: 4-(trans-4-n-octylcyclohexyl)-1-[2-(4-cyanophenyl)ethyl]cyclohexene
Compound No. 351: 4-(trans-4-n-nonylcyclohexyl)-1-[2-(4-cyanophenyl)ethyl]cyclohexene
Compound No. 352: 4-(trans-4-n-decylcyclohexyl)-1-[2-(4-cyanophenyl)ethyl]cyclohexene
Compound No. 353: 4-[2-(trans-4-ethylcyclohexyl)ethyl]-1-[2-(4-cyanophenyl)ethyl]cyclohexene
Compound No. 354: 4-[2-(trans-4-n-propylcyclohexyl)ethyl]-1-[2-(4-cyanophenyl)ethyl]cyclohexene The following compounds were obtained which were represented by the formula [Ibb] wherein Y=H.

Compound No. 355: 4-[2-(trans-4-n-butylcyclohexyl)ethyl]-1-[2-(4-cyanophenyl)ethyl]cyclohexene
Compound No. 356: 4-[2-(trans-4-n-pentylcyclohexyl)ethyl]-1-[2-(4-cyanophenyl)ethyl]cyclohexene
Compound No. 357: 4-[2-(trans-4-n-hexylcyclohexyl)ethyl]-1-[2-(4-cyanophenyl)ethyl]cyclohexene
Compound No. 358: 4-[2-(trans-4-n-heptylcyclohexyl)ethyl]-1-[2-(4-cyanophenyl)ethyl]cyclohexene
Compound No. 359: 4-[2-(trans-4-n-octylcyclohexyl)ethyl]-1-[2-(4-cyanophenyl)ethyl]cyclohexene
Compound No. 360: 4-[2-(trans-4-n-nonylcyclohexyl)ethyl]-1-[2-(4-cyanophenyl)ethyl]cyclohexene
Compound No. 361: 4-[2-(trans-4-n-decylcyclohexyl)ethyl]-1-[2-(4-cyanophenyl)ethyl]cyclohexene

EXAMPLE 21

Synthesis of 4-n-pentyl-1-[2-(4-cyanophenyl)ethyl]cyclohexene [Compound No. 362 (in the formula [Ibc], Y=H and R=$C_5H_{11}$]:

The same procedure as in Example 19 was effected except that 4-(trans-4-n-pentylcyclohexyl)cyclohexanone used in Example 19 was replaced with 4-n-pentylcyclohexanone, in order to obtain the desired compound.

m.p. 25° C. and[clp. 13° C.

EXAMPLE 22

The same procedure as in Example 19 was effected except that 4-(trans-4-n-pentylcyclohexyl)cyclohexanone used in Example 19 was replaced with a suitable cyclohexanone derivative, in order to obtain the following compounds (in the formula [Ibc], Y=H).

Compound No. 363: 4-ethyl-1-[2-(4-cyanophenyl)ethyl]cyclohexene
Compound No. 364: 4-n-propyl-1-[2-(4-cyanophenyl)ethyl]cyclohexene
Compound No. 365: 4-n-butyl-1-[2-(4-cyanophenyl)ethyl]cyclohexene
Compound No. 366: 4-n-hexyl-1-[2-(4-cyanophenyl)ethyl]cyclohexene
Compound No. 367: 4-n-heptyl-1-[2-(4-cyanophenyl)ethyl]cyclohexene
Compound No. 368: 4-n-octyl-1-[2-(4-cyanophenyl)ethyl]cyclohexene
Compound No. 369: 4-n-nonyl-1-[2-(4-cyanophenyl)ethyl]cyclohexene
Compound No. 370: 4-n-decyl-1-[2-(4-cyanophenyl)ethyl]cyclohexene

EXAMPLE 23

Synthesis of 4-(trans-4-n-pentylcyclohexyl)-1-[2-(3-fluoro-4-cyanophenyl)ethyl]cyclohexene [Compound No. 371 (in the formula [Iba], Y=F and R=$C_5H_{11}$]:

(i) Synthesis of 4-(trans-4-n-pentylcyclohexyl)cyclohexylidene- 2-(3-fluoro-4-bromophenyl)ethane:

At a temperature of −50° C., 5.6 g of potassium tert-butoxide was added into a 500-ml three-necked flask in which 27.2 g of 2-(3-fluoro-4-bromophenyl)ethyltriphenylphosphonium bromide and 100 ml of THF were present. The resulting solution was then stirred at −50° C. for 1 hour, and 50 ml of a THF solution containing 10.0 g of 4-(trans-4-n-pentylcyclohexyl)cyclohexanone was added dropwise to the solution. Afterward, the solution was stirred for 10 hours, raising its temperature to room temperature gradually. To the solution was added 300 ml of water, followed by stirring, and extraction was then carried out with 200 ml of toluene. The resulting organic layer was washed with 300 ml of water twice, and then dried over anhydrous magnesium sulfate and concentrated. To the thus concentrated solution was then added 300 ml of heptane to deposit crystals, and the latter were removed therefrom by filtration. The filtrate was passed through a column packed with silica gel and then concentrated. Next, the solution was recrystallized from a mixed solvent of an alcohol and ethyl acetate and then dried in order to obtain 10.5 g of the desired compound.

(ii) Synthesis of 4-(trans-4-n-pentylcyclohexyl)-1-[2-(3-fluoro-4-bromophenyl)ethyl]cyclohexene:

To a three-necked flask in which 6.6 of metachloroperbenzoic acid, 5.3 g of potassium carbonate and 70 ml of chloroform were present was added dropwise 30 ml of a chloroform solution containing 8.3 g of the compound obtained in the above-mentioned process (i) at 10° C. The solution was stirred for 3 hours, and insoluble matters were then removed therefrom by filtration. Afterward, 50 ml of an aqueous sodium thiosulfate solution was added to the solution. After the removal of a water layer, the solution was then washed with 50 ml of a 1 N aqueous sodium hydroxide solution, and water washing was continued until wash liquid became neutral. The solution was then dried over anhydrous magnesium sulfate and then concentrated, thereby obtaining 9.2 g of an oily material.

Afterward, 30 ml of a THF solution containing the thus obtained material was added dropwise at 20° C. to a 200-ml three necked flask in which 29 ml of a 1 mol solution of lithium hydride triethylboron was present. After stirring for one day, 100 ml of water and 100 ml of toluene were added thereto, and a water layer was then removed therefrom. The resulting organic layer was washed with 100 mol of water twice, and it was then dried over anhydrous magnesium sulfate and concentrated.

To the concentrated solution were added 0.1 g of paratoluenesulfonic acid monohydrate and 50 ml of toluene, followed by heating under reflux for 1 hour. At this time, a drainage pipe was used to remove water formed by azeotropy. After cooling, 50 ml of a 0.5 N aqueous sodium hydroxide solution and 50 ml of heptane were added to the solution, followed by removing a water layer. Afterward, the solution was washed with 50 ml of a saturated sodium chloride solution three times, and it was then dried over anhydrous magnesium sulfate and concentrated. The thus treated solution was passed through a silica gel-packed column by the use of a heptane solvent, and the used heptane was then distilled off, whereby 5.8 g of white crystals was obtained. The thus obtained crystals were further recrystallized from a mixed solvent of an alcohol and heptane, and then dried in order to prepare 3.6 g of the desired compound. The structure of the product was confirmed by NMR.

(iii) Synthesis of 4-(trans-4-n-pentylcyclohexyl)-1-(2-(3-fluoro-4-cyanophenyl)ethyl)cyclohexene:

In a 100-ml three-necked flask were placed 3.6 g of the compound obtained in the above-mentioned process (ii), 0.9 g of copper cyanide (I) and 30 ml of DMF, followed by heating under reflux for 24 hours. After standing, 20 ml of aqueous ammonia and 50 ml of toluene were added to the solution, and a water layer was then removed therefrom. An organic layer was then filtered to remove insoluble matters therefrom. The resulting filtrate was washed with 50 ml of 2 N hydrochloric acid and then 50 ml of an aqueous saturated sodium hydrogencarbonate solution in this order, and it was further washed with water until the wash liquid became neutral. Afterward, the solution was dried over anhydrous magnesium sulfate, and the used solvent was then distilled off. The residue was passed through a silica gel column by the use of a mixed solvent of heptane and toluene at a ratio of 1:1. After concentration, the solution was recrystallized from a heptane solvent and then dried, thereby obtaining 1.6 g of the desired compound. The structure of the product was confirmed by NMR.

EXAMPLE 24

The same procedure as in Example 19 was effected except that 2-(4-bromophenyl)ethyltriphenylphosphonium bromide used in Example 19 was replaced with 2-(3-fluoro-4-bromophenyl)ethyltriphenylphosphonium bromide and 4-(trans-4-n-pentylcyclohexyl)cyclohexanone was replaced with a suitable cyclohexanone derivative, in order to obtain the following compounds (in the formula [Iba], Y=F).

Compound No. 372: 4-(trans-4-ethylcyclohexyl)-1-[2-(3-fluoro-4-cyanophenylethyl]cyclohexene Compound No. 373: 4-(trans-4-n-propylcyclohexyl)-1-[2-(3-fluoro-4-cyanophenyl)ethyl]cyclohexene Compound No. 374: 4-(trans-4-n-butylcyclohexyl)-1-[2-(3-fluoro-4-cyanophenyl)ethyl]cyclohexene Compound No. 375: 4-(trans-4-n-hexylcyclohexyl)-1-[2-(3-fluoro-4-cyanophenyl)ethyl]cyclohexene Compound No. 376: 4-(trans-4-n-heptylcyclohexyl)-1-[2-(3-fluoro-4-cyanophenyl)ethyl]cyclohexene Compound No. 377: 4-(trans-4-n-octylcyclohexyl)-1-[2-(3-fluoro-4-cyanophenyl)ethyl]cyclohexene Compound No. 378: 4-(trans-4-n-nonylcyclohexyl)-1-[2-(3-fluoro-4-cyanophenyl)ethyl]cyclohexene Compound No. 379: 4-(trans-4-n-decylcyclohexyl)-1-[2-(3-fluoro-4-cyanophenyl)ethyl]cyclohexene The following compounds were obtained which were represented by the formula [Ibb] wherein Y=F.

Compound No. 380: 4-[2-(trans-4-ethylcyclohexyl)ethyl]-1-[2-(3-fluoro-4-cyanophenyl)ethyl]cyclohexene Compound No. 381: 4-[2-(trans-4-n-propylcyclohexyl)ethyl]-1-[2-(3-fluoro-4-cyanophenyl)ethyl]cyclohexene Compound No. 382: 4-[2-(trans-4-n-butylcyclohexyl)ethyl]-1-[2-(3-fluoro-4-cyanophenyl)ethyl]cyclohexene Compound No. 383: 4-[2-(trans-4-n-pentylcyclohexyl)ethyl]-1-[2-(3-fluoro-4-cyanophenyl)ethyl]cyclohexene Compound No. 384: 4-[2-(trans-4-n-hexylcyclohexyl)ethyl]-1-[2-(3-fluoro-4-cyanophenyl)ethyl]cyclohexene Compound No. 385: 4-[2-(trans-4-n-heptylcyclohexyl)ethyl]-1-[2-(3-fluoro-4-cyanophenyl)ethyl]cyclohexene Compound No. 386: 4-[2-(trans-4-n-octylcyclohexyl)ethyl]-1-[2-(3-fluoro-4-cyanophenyl)ethyl]cyclohexene Compound No. 387: 4-[2-(trans-4-n-nonylcyclohexyl)ethyl]-1-[2-(3-fluoro-4-cyanophenyl)ethyl]cyclohexene Compound No. 388: 4-[2-(trans-4-n-decylcyclohexyl)ethyl]-1-[2-(3-fluoro-4-cyanophenyl)ethyl]cyclohexene

EXAMPLE 25

The same procedure as in Example 19 was effected except that 2-(4-bromophenyl)ethyltriphenylphosphonium bromide used in Example 19 was replaced with 2-(3-fluoro-4-bromophenyl)ethyltriphenylphosphonium bromide and 4-(trans-4-n-pentylcyclohexyl)-cyclohexanone was replaced with a suitable cyclohexanone derivative, in order to obtain the following compounds (in the formula [Ibc], Y=F).

Compound No. 389: 4-ethyl-1-[2-(3-fluoro-4-cyanophenyl)ethyl]cyclohexene
Compound No. 390: 4-n-propyl-1-[2-(3-fluoro-4-cyanophenyl)ethyl]cyclohexene
Compound No. 391: 4-n-butyl-1-[2-(3-fluoro-4-cyanophenyl)ethyl]cyclohexene
Compound No. 392: 4-n-pentyl-1-[2-(3-fluoro-4-cyanophenyl)ethyl]cyclohexene
Compound No. 393: 4-n-hexyl-1-[2-(3-fluoro-4-cyanophenyl)ethyl]cyclohexene
Compound No. 394: 4-n-heptyl-1-[2-(3-fluoro-4-cyanophenyl)ethyl]cyclohexene
Compound No. 395: 4-n-octyl-1-[2-(3-fluoro-4-cyanophenyl)ethyl]cyclohexene
Compound No. 396: 4-n-nonyl-1-[2-(3-fluoro-4-cyanophenyl)ethyl]cyclohexene
Compound No. 397: 4-n-decyl-1-[2-(3-fluoro-4-cyanophenyl)ethyl]cyclohexene

EXAMPLE 26 (USE EXAMPLE)

In a liquid crystal composition A comprising

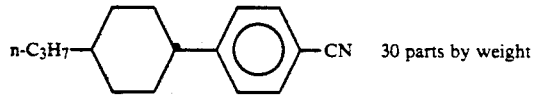
n-C$_3$H$_7$—〈cyclohexyl〉—〈phenyl〉—CN   30 parts by weight

n-C$_5$H$_{11}$—〈cyclohexyl〉—〈phenyl〉—CN   40 parts by weight

n-C$_7$H$_{15}$—〈cyclohexyl〉—〈phenyl〉—CN   30 parts by weight clp. was 52.3° C., Δε was 10.7, Δn was 0.119, and the viscosity at 20° C. was 22 cp. When 15 parts by weight of the compound (No. 1) referred to in Example 1 of the present invention was added to 85 parts by weight of this liquid crystal composition A, a novel liquid crystal composition was obtained in which clp. rose up to 62.6° C. and the viscosity at 20° C. fell to 21 cp. Furthermore, even when the liquid crystal composition was allowed to stand at −20° C. for 40 days, a nematic phase was maintained without depositing any crystals.

EXAMPLES 27 TO 32

In each example, 15 parts by weight of the compound represented by the formula [I] which was the compound of the present invention was added to 85 parts by weight of the liquid crystal composition A, in order to obtain a novel liquid crystal composition. Values of clp. of the obtained compositions are set forth in Table 1.

TABLE 1

| Example No. | Compound No. | clp. (°C.) |
|---|---|---|
| 27 | 4 | 63.0 |
| 28 | 34 | 65.4 |
| 29 | 61 | 57.0 |
| 30 | 245 | 58.1 |
| 31 | 253 | 54.1 |
| 32 | 344 | |

What is claimed is:

1. A cyclohexenylethane compound represented by the formula [I]

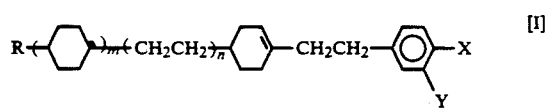

wherein R is an alkyl group having 1 to 10 carbon atoms, X is an alkyl group or an alkoxy group having 1 to 10 carbon atoms, a cyano group, a bromine atom or a fluorine atom, Y is a hydrogen atom or a fluorine atom, m is 0 or 1, and n is 0 or 1.

2. A cyclohexenylethane compound according to claim 1 which is represented by the formula [Iaa]

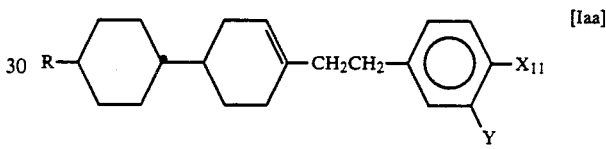

wherein $X_{11}$ is an alkyl group or an alkoxy group having 1 to 10 carbon atoms, and R and Y are as defined in claim 1.

3. A cyclohexenylethane compound according to claim 1 which is represented by the formula [Iab]

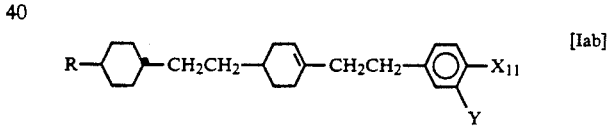

wherein $X_{11}$ is an alkyl group or an alkoxy group having 1 to 10 carbon atoms, and R and Y are as defined in claim 1.

4. A cyclohexenylethane compound according to claim 1 which is represented by the formula [Iac]

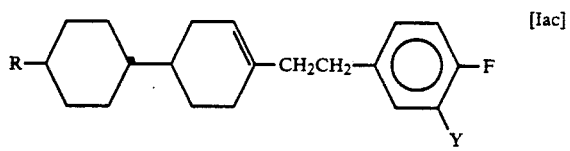

wherein, R and Y are as defined in claim 1.

5. A cyclohexenylethane compound according to claim 1 which is represented by the formula [Iad]

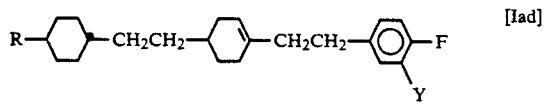

wherein R and Y are as defined in claim 1.

6. A cyclohexenylethane compound according to claim 1 which is represented by the formula [Iba]

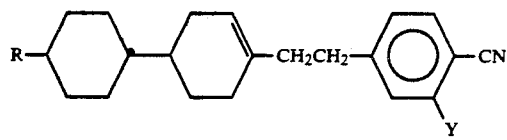

wherein R and Y are as defined in claim 1.

7. A cyclohexenylethane compound according to claim 1 which is represented by the formula [Ibb]

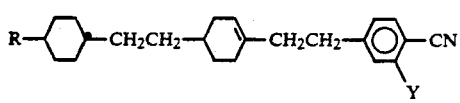

wherein, R and Y are as defined in claim 1.

8. A cyclohexenylethane compound according to claim 1 which is represented by the formula [Iae]

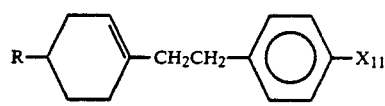

wherein $X_{11}$ is an alkyl group or an alkoxy group having 1 to 10 carbon atoms, and R is as defined in claim 1.

9. A cyclohexenylethane compound according to claim 1 which is represented by the formula [Iaf]

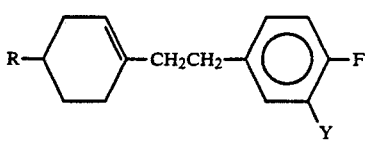

wherein R and Y are as defined in claim 1.

10. A cyclohexenylethane compound according to claim 1 which is represented by the formula [Ibc]

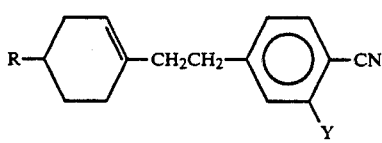

wherein R and Y are as defined in claim 1.

11. A liquid crystal composition which comprises at least two components, at least one of these components being the cyclohexenylethane compound described in claim 1.

* * * * *